US011414493B2

(12) United States Patent
Jung et al.

(10) Patent No.: US 11,414,493 B2
(45) Date of Patent: Aug. 16, 2022

(54) AGLYCOSYLATED ANTIBODY FC REGION FOR TREATING CANCER

(71) Applicant: KOOKMIN UNIVERSITY INDUSTRY ACADEMY COOPERATION FOUNDATION, Seoul (KR)

(72) Inventors: Sang Taek Jung, Gyeonggi-do (KR); Migyeong Jo, Gyeonggi-do (KR)

(73) Assignee: KOOKMIN UNIVERSITY INDUSTRY ACADEMY COOPERATION FOUNDATION, Seoul (KR)

(*) Notice: Subject to any disclaimer, the term of this patent is extended or adjusted under 35 U.S.C. 154(b) by 474 days.

(21) Appl. No.: 16/345,062

(22) PCT Filed: Aug. 22, 2017

(86) PCT No.: PCT/KR2017/009153
§ 371 (c)(1),
(2) Date: Apr. 25, 2019

(87) PCT Pub. No.: WO2018/079997
PCT Pub. Date: May 3, 2018

(65) Prior Publication Data
US 2019/0352396 A1 Nov. 21, 2019

(30) Foreign Application Priority Data

Oct. 27, 2016 (KR) .................. 10-2016-0141118
Nov. 8, 2016 (KR) .................. 10-2016-0148002

(51) Int. Cl.
C07K 1/00 (2006.01)
A61K 39/00 (2006.01)
C07K 16/28 (2006.01)
A61P 35/00 (2006.01)
A61K 39/395 (2006.01)

(52) U.S. Cl.
CPC ...... C07K 16/283 (2013.01); A61K 39/39591 (2013.01); A61P 35/00 (2018.01); C07K 2317/41 (2013.01); C07K 2317/52 (2013.01)

(58) Field of Classification Search
None
See application file for complete search history.

(56) References Cited

U.S. PATENT DOCUMENTS

| 6,737,056 B1 * | 5/2004 | Presta ............... C07K 16/4291 424/133.1 |
| 8,815,237 B2 | 8/2014 | Wittrup et al. |
| 8,952,132 B2 * | 2/2015 | Georgiou ............... A61P 29/00 530/350 |
| 2005/0054832 A1 | 3/2005 | Lazar et al. |
| 2009/0136936 A1 | 5/2009 | Georgiou et al. |
| 2010/0184959 A1 | 7/2010 | Guler-Gane et al. |

FOREIGN PATENT DOCUMENTS

| KR | 101926263 | 12/2018 | |
| WO | 2008092117 | 7/2008 | |
| WO | WO-2015054039 A1 * | 4/2015 | ............. C07K 16/32 |

OTHER PUBLICATIONS

Jo, "Isolation of Aglycosylated IgG Fc Variants for NK Cell-Mediated Tumor Cell Killing", Graduate School of Kookmin University, Master's Thesis, Dec. 2015, 53 pages.
Köhler et al., "Continuous Cultures of Fused Cells Secreting Antibody of Predifined Specificity", Nature, vol. 256, Aug. 7, 1975, 495-497.
Boruchov et al., "Activating and inhibatory IgG Fc receptors on human DCs mediate opposing functions", The Journal of Clinical Investigation, vol. 115, No. 10, Oct. 2005, 2914-2923.
Deisenhofer, "Crystallographic Refinement and Atomic Models of a Human Fc Fragment and Its Complex with Fragment B of Protein A from Staphylococcus aureus at 2.9- and 2.8-A Resolution", American Chemical Society, vol. 20, No. 9, Apr. 28, 1981, 2361-2370.
Ausubel et al., "Current Protocols in Molecular Biology", John Wiley & Sons, Dec. 4, 2013.
Gomaa, A.A., et al., "Amelioration of experimental metabolic syndrome induced in rats by orlistat and Corchorus olitorius leaf extract; role of adipo/cytokines," Journal of Pharmacy and Pharmacology, 2019, vol. 71, pp. 281-291.

* cited by examiner

Primary Examiner — Chun W Dahle
(74) Attorney, Agent, or Firm — Duane Morris LLP; Gregory M. Lefkowitz; Brandon A. Chan

(57) ABSTRACT

The present disclosure relates to a polypeptide containing an Fc domain in which a part of an amino acid sequence of a human antibody Fc domain is substituted with another amino acid sequence, or an aglycosylated antibody containing the same. The Fc domain of the present disclosure is optimized by substituting a part of an amino acid sequence of a wild-type Fc domain with another amino acid sequence. Therefore, it is useful in treatment of cancer due to superior selective binding ability to FcγRIIIa among Fc receptors, and can be prepared as a homogeneous aglycosylated antibody through bacterial culture.

13 Claims, 15 Drawing Sheets
Specification includes a Sequence Listing.

AGLYCOSYLATED ANTIBODY FC REGION FOR TREATING CANCER

CROSS-REFERENCE TO RELATED APPLICATIONS

This application is a § 371 national stage entry of International Application No. PCT/KR2017/009153, filed on Aug. 22, 2017, which claims priority to Korean Patent Application No. 10-2016-0141118, filed Oct. 27, 2016 and Korean Patent Application No. 10-2016-0148002, filed Nov. 8, 2016, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jul. 29, 2019, is named G1035-14601_SeqList.txt and is 25,577 bytes in size.

TECHNICAL FIELD

The present disclosure relates to an aglycosylated antibody Fc region useful for cancer treatment, and a method for preparing the same.

BACKGROUND ART

With the development of biotechnology such as genetic recombination, cell culturing, etc. globally, researches on the structure and function of proteins have been carried out actively. They significantly contribute to the improvement in quality of life by promoting the understanding of biological phenomena and elucidating the mechanism of various diseases, thereby paving the way for effective diagnosis and treatment of diseases. In particular, since the development of hybridoma technology, which produces monoclonal antibodies by fusing B cells with myeloma cells, in 1975 (Kohler and Milstein, *Nature*, 256: 495-497, 1975), researches and developments are carried out actively on immunotherapy using therapeutic antibodies in clinical fields such as cancer, autoimmune disease, inflammation, cardiovascular disease, infection, etc.

Therapeutic antibodies are considered one of the most effective cancer therapies because they show very high specificity for targets as compared to the existing small-molecule drugs, show low biological toxicity and few side effects, and have superior plasma half-life of about 3 weeks. Indeed, big global pharmaceutical companies and research institutes are accelerating their pace in the research and development of therapeutic antibodies which effectively remove carcinogenic factors and cancer cells by specifically binding thereto. The leading pharmaceutical companies developing therapeutic antibodies include Roche, Amgen, Johnson & Johnson, Abbott, BMS, etc. Particularly, Roche is making a considerable profit with the three representative therapeutic antibodies, Herceptin, Avastin and Rituxan, which achieved about 19.5 billion dollars of sales in 2012 globally, and is leading the world antibody drug market. Johnson & Johnson, the developer of Remicade, is also growing fast in the global antibody market. Other pharmaceutical enterprises such as Abbott, BMS, etc. are also known to have many therapeutic antibodies in the last stage of development. As a consequence, biopharmaceuticals including therapeutic antibodies, which are specific for target diseases and have few side effects, are quickly taking place of small-molecule drugs that have predominated in the global pharmaceutical market.

One of the most important mechanisms of therapeutic antibodies is to recruit immune cells and direct them to target antigens. The Fc domain of the antibody plays a critical role in the recruiting of immune cells and antibody-dependent cell-mediated cytotoxicity (ADCC). In particular, the ADCC function of the antibody is dependent on the interaction with the Fc receptors (FcR) present on the surface of many cells. Human Fc receptors are classified into 5 types. The type of recruited immune cells is determined by Fc receptor to which the antibody is bound. Accordingly, an attempt to modify the antibody to recruit specific cells is very important in the therapeutic field.

However, most attempts that have been made up to now were to modify the Fc domain by using IgG molecules expressed by mammals. The mammalian antibodies are glycosylated. Glycan chains appended at the Fc region of the glycosylated antibody allows the antibody to bind to the Fc receptor by stabilizing the structure of the protein. In contrast, the aglycosylated antibodies produced in bacteria lack the glycan chains linked to the Fc region. Therefore, they cannot bind to the Fc receptors and do not exhibit the ADCC function. Therefore, if an aglycosylated antibody that can bind to the Fc receptor is developed, the antibody can be produced by using bacteria, rather than animal cells, which will bring cost reduction.

In addition, there is a problem that, although the mammalian antibody with the Fc region modified has increased binding capability to a specific Fc receptor, undesired immune response can occur because it maintains binding capability to other Fc receptors too. There exist five main FcγRs for human. Four among the receptors induce immune activation or inflammatory response, and FcγRIIb induces immune inhibition or anti-inflammatory response. Most of naturally produced antibodies or recombinant glycosylated antibodies bind to both the activating and inhibitory Fc receptors. The ADCC inducing ability of an antibody depends on the ratio of its ability to bind to activating FcγR and the ability to bind to inhibitory FcγRIIb (A/I ratio) (Boruchov et al, *J Clin Invest*, 115(10): 2914-23, 2005). However, because FcγRIIb shares 96% sequence identity with activating FcγR, the attempt to increase the A/I ratio by introducing genetic mutation to the glycosylated antibody fails to bear much fruit.

Meanwhile, among the several immune cells involved in the cancer cell killing mechanism using therapeutic IgG antibodies used clinically at present, natural killer cells (NK cells) are known to have the most powerful cancer cell killing effect. Unlike other immune cells (e.g., monocytes, macrophages and dendritic cells), the NK cells express FcγRIIIa on their surfaces and do not express FcγRI, FcγRIIa, FcγRIIb and FcγRIIIb. Accordingly, in order to maximize the cancer cell killing mechanism unlike the existing therapeutic antibodies, it is essential to improve affinity for FcγRIIIa expressed the surface of the NK cells by optimizing the Fc region of the IgG antibody.

The description of the background art given above is only for enhancing the understanding of the background of the present disclosure and should not be regarded that it is known to those of ordinary skill in the related art.

DISCLOSURE

Technical Problem

The inventors of the present disclosure have made consistent efforts to develop an aglycosylated antibody having no heterogeneity issue of the existing glycosylated antibodies and having improved binding ability for FcγRIIIa expressed on the surface of NK cells. As a result, they have identified that binding ability to FcγRIIIa selectively among Fc receptors is improved greatly through optimization by substituting a part of an amino acid sequence of a wild-type Fc domain with another amino acid sequence and, through this, the cancer cell killing effect of NK cells is enhanced.

The present disclosure is directed to providing a polypeptide containing an Fc domain in which a part of an amino acid sequence of a human antibody Fc domain is substituted with another amino acid sequence.

The present disclosure is also directed to providing an aglycosylated antibody containing the polypeptide.

The present disclosure is also directed to providing a nucleotide molecule encoding the polypeptide.

The present disclosure is also directed to providing a vector containing the nucleotide molecule.

The present disclosure is also directed to providing a host cell containing the vector.

The present disclosure is also directed to providing a composition containing the polypeptide, the aglycosylated antibody, the nucleotide molecule or the vector.

The present disclosure is also directed to providing a method for preventing or treating cancer, which includes a step of administering the polypeptide, the aglycosylated antibody, the nucleotide molecule or the vector.

The present disclosure is also directed to providing a method for preparing the polypeptide or the aglycosylated antibody.

The present disclosure is also directed to providing a method for screening a polypeptide containing an Fc domain binding to FcγRIIIa.

Other purposes and advantages of the present disclosure will be apparent from the following detailed description, the drawings, and the claims.

Technical Solution

In an aspect, the present disclosure provides a polypeptide containing an Fc domain in which a part of an amino acid sequence of a human antibody Fc domain is substituted with another amino acid sequence.

The inventors of the present disclosure have made consistent efforts to develop an aglycosylated antibody having no heterogeneity problem of the existing glycosylated antibodies and having improved binding ability for FcγRIIIa expressed on the surface of NK cells. As a result, they have identified that binding ability to FcγRIIIa selectively among Fc receptors is improved greatly through optimization by substituting a part of an amino acid sequence of a wild-type Fc domain with another amino acid sequence and, through this, the cancer cell killing effect of NK cells is enhanced.

An antibody is a protein which binds specifically to a particular antigen. A natural antibody is a heterodimeric glycoprotein of about 150,000 daltons, which commonly consists of two identical light chains (L) and two identical heavy chains (H).

The human antibodies used in the present disclosure consist of five main classes of IgA, IgD, IgE, IgG and IgM. Specifically, it is IgG. An antibody digested by papain yields two Fab fragments and one Fc fragment. The Fc region is produced from the human IgG molecule as the N-terminal of Cys 226 is cleaved by papain (Deisenhofer, *Biochemistry* 20: 2361-2370, 1981).

The antibody Fc domain may be an Fc domain of the IgA, IgM, IgE, IgD or IgG antibody, or a variant thereof. In an exemplary embodiment, the domain is an Fc domain of the IgG antibody (e.g., Fc domain of the IgG1, IgG2a, IgG2b, IgG3 or IgG4 antibody). In an exemplary embodiment, the Fc domain may be the IgG1 Fc domain (e.g., the Fc domain of anti-HER2 antibody, more specifically the Fc domain of trastuzumab). The polypeptide containing the Fc domain of the present disclosure may be not glycosylated at all, or only a part of the polypeptide (e.g., the Fc domain) may be glycosylated. The polypeptide may further contain one or more region derived from an antibody, in addition to the Fc domain. Additionally, the polypeptide may further contain an antibody-derived antigen-binding domain. Also, multiple polypeptides may form an antibody or an antibody-type protein.

In the present disclosure, the numbering of the amino acid residues of the antibody Fc domain follows the commonly used Kabat numbering system (Kabat et al., "Sequences of Proteins of Immunological Interest", 5th Ed., U.S. Department of Health and Human Services, NIH Publication No. 91-3242, 1991).

In a specific exemplary embodiment of the present disclosure, the substituted Fc domain of the present disclosure includes the following 8 amino acid substitutions according to the Kabat numbering system: S298G, T299A, K326I, A327Y, L328G, E382V, N390D and M428L.

In an exemplary embodiment of the present disclosure, the aglycosylated Fc domain is mutated to bind to one or more of FcγRIa, FcγRIIa, FcγRIIb, FcγRIIc, FcγRIIIa, FcγRIIIb or FcαRI. The mutated aglycosylated Fc domain may have 10% or lower, 20% or lower, 30% or lower, 40% or lower, 50% or lower, 60% or lower, 70% or lower, 80% or lower, 90% or lower, 100%, 2 times or higher, 3 times or higher, 4 times or higher, 5 times or higher, 6 times or higher, 7 times or higher, 8 times or higher, 9 times or higher, 10 times or higher or 20 times or higher binding ability to one or more of the above Fc receptors as compared to the wild-type glycosylated Fc domain.

In a specific exemplary embodiment of the present disclosure, the Fc domain contained in the polypeptide of the present disclosure has improved binding ability for FcγRIIIa as compared to the Fc domain not substituted with the above 8 amino acids.

According to the examples of the present disclosure, the Fc domain with only S298G, T299A, N390D, E382V and M428L substituted (Fc1004, U.S. Pat. No. 8,952,132) does not bind to FcγRIIIa like the wild-type Fc domain, and the Fc domain with only T299A, K326I, A327Y and L328G substituted (A/IYG, U.S. Pat. No. 8,815,237) also shows very little increase in the binding ability for FcγRIIIa as compared to the wild-type Fc domain. In contrast, the Fc domain of the present disclosure, which includes the above 8 amino acid substitutions, shows significantly improved binding ability for FcγRIIIa as compared to the wild-type Fc domain, Fc1004 or A/IYG (Examples 3 and 4).

In a specific exemplary embodiment of the present disclosure, the amino acid substitution of the present disclosure includes one or more additional amino acid substitution selected from a group consisting of C226R, F243L, K246E, T250I, I253N, V264E, T307S, C347R, T350A, S400T and N421S according to the Kabat numbering system.

In a specific exemplary embodiment of the present disclosure, the Fc domain with 9 or more amino acids substituted of the present disclosure has improved binding ability for FcγRIIIa as compared to the Fc domain with only the 8 amino acids of S298G, T299A, K326I, A327Y, L328G, E382V, N390D and M428L substituted.

According to the examples of the present disclosure, the Fc domain with 9 or more amino acids substituted has 40% or more increased binding ability for FcγRIIIa as compared to the Fc domain with only the 8 amino acids substituted (MG42: 40% or more; MG61: 50% or more; MG54, MG59 and MG86: 200% or more; MG14 and MG87: 300% or more; MG48: 500% or more; FIGS. 6A-6C).

In a specific exemplary embodiment of the present disclosure, the substituted Fc domain of the present disclosure includes the following 9 amino acid substitutions according to the Kabat numbering system: S298G, T299A, T307S, K326I, A327Y, L328G, E382V, N390D and M428L.

In a specific exemplary embodiment of the present disclosure, the substituted Fc domain of the present disclosure includes the following 9 amino acid substitutions according to the Kabat numbering system: S298G, T299A, K326I, A327Y, L328G, C347R, E382V, N390D and M428L.

In a specific exemplary embodiment of the present disclosure, the substituted Fc domain of the present disclosure includes the following 10 amino acid substitutions according to the Kabat numbering system: V264E, S298G, T299A, K326I, A327Y, L328G, T350A, E382V, N390D and M428L.

In a specific exemplary embodiment of the present disclosure, the substituted Fc domain of the present disclosure includes the following 10 amino acid substitutions according to the Kabat numbering system: T250I, I253N, S298G, T299A, K326I, A327Y, L328G, E382V, N390D and M428L.

In a specific exemplary embodiment of the present disclosure, the substituted Fc domain of the present disclosure includes the following 10 amino acid substitutions according to the Kabat numbering system: V264E, S298G, T299A, K326I, A327Y, L328G, E382V, N390D, N421S and M428L.

In a specific exemplary embodiment of the present disclosure, the substituted Fc domain of the present disclosure includes the following 11 amino acid substitutions according to the Kabat numbering system: V264E, S298G, T299A, K326I, A327Y, L328G, T350A, E382V, N390D, N421S and M428L.

In a specific exemplary embodiment of the present disclosure, the substituted Fc domain of the present disclosure includes the following 11 amino acid substitutions according to the Kabat numbering system: C226R, F243L, K246E, S298G, T299A, K326I, A327Y, L328G, E382V, N390D and M428L.

In another aspect, the present disclosure provides an aglycosylated antibody containing the polypeptide.

In the present disclosure, the term "antibody" means a polyclonal antibody, a monoclonal antibody, a human antibody and a humanized antibody, and fragments thereof.

All the currently commercialized therapeutic antibodies are produced through animal cell culturing. When the antibodies are produced, the antibody proteins are modified by various sugar (carbohydrate) variants. In this regard, glycan heterogeneity causes variation in the efficacy and stability of the antibodies, and a lot of cost is required for purification, analysis and quality control (QC) during the preparation process of the antibodies.

When compared with the glycosylated antibodies requiring the expensive animal cell culturing system, aglycosylated antibodies can be produced in large scale in bacteria and exhibit superior excellence in terms of speed and cost. However, whereas the N-linked glycan formed at the Asn297 amino acid of the glycosylated antibody plays a critical role in the structure and function of the antibody, the aglycosylated antibody Fc region has a closed structure with the CH2 region closed or a very flexible structure unlike the glycosylated antibody Fc produced in animal cells. Therefore, the aglycosylated antibody cannot bind to FcγRIIIa, which plays a critical role in the recruiting and activation of NK cells, and fails to exhibit the cancer cell killing effect.

In a specific exemplary embodiment of the present disclosure, through optimization of the aglycosylated antibody Fc region (8 amino acid substitutions of S298G, T299A, K326I, A327Y, L328G, E382V, N390D and M428L), the antibody exhibits maximized cancer cell killing mechanism due to improved binding ability for FcγRIIIa expressed on the surface of NK cells, while being capable of produced in bacteria at low cost without the glycan heterogeneity problem.

In another aspect, the present disclosure provides a nucleotide molecule encoding the polypeptide, a vector containing the nucleotide molecule, or a host cell containing the vector.

In another aspect, the present disclosure provides a method for preparing a polypeptide containing a human antibody Fc domain, which includes:

a) a step of culturing a host cell containing a vector containing a nucleotide molecule encoding the polypeptide described above; and b) a step of recovering the polypeptide expressed by the host cell.

In another aspect, the present disclosure provides a method for preparing an aglycosylated antibody, which includes:

a) a step of culturing a host cell expressing an aglycosylated antibody containing the polypeptide described above; and b) a step of purifying the antibody expressed by the host cell.

The nucleotide molecule of the present disclosure may be an isolated or recombinant nucleotide molecule, and includes not only single-chain and double-chain DNA and RNA but also complementary sequences corresponding thereto. If the "isolated nucleotide" is a nucleotide isolated from a natural origin, the nucleotide is a nucleotide separated from nearby gene sequences existing in the isolated genome of an individual. For nucleotides, e.g., PCR products, cDNA molecules or oligonucleotides, enzymatically or chemically synthesized from a template, the nucleotides produced from these procedures may be understood as the isolated nucleotide molecules. An isolated nucleotide molecule may be a component of a fragment or a lager nucleotide construct. A nucleotide is "operably linked" when it is placed into a functional relationship with another nucleotide sequence. For example, DNA for a presequence or secretory leader is operably linked to DNA for a polypeptide if it is expressed as a preprotein that participates in the secretion of the polypeptide, a promoter or enhancer is operably linked to a coding sequence if it affects the transcription of the polypeptide sequence, or a ribosome binding site is operably linked to a coding sequence if it is positioned so as to facilitate translation. Generally, "operably linked" means that the DNA sequences being linked are contiguous, and, in the case of a secretory leader, contiguous and present in the same reading frame. However, enhancers do not have to be contiguous. The linking is accomplished by ligation at convenient restriction enzyme sites. If such sites do not exist, synthetic oligonucleotide adaptors or linkers are used in accordance with common methods.

In the present disclosure, the term "vector" refers to a carrier capable of inserting a nucleotide sequence for introduction into a cell capable of replicating the nucleotide sequence. The nucleotide sequence may be exogenous or heterologous. The vector may be a plasmid, a cosmid or a virus (e.g., a bacteriophage), although not being limited thereto. Those skilled in the art can construct the vector according to the standard recombination technology (Maniatis, et al., *Molecular Cloning*, A Laboratory Manual, Cold Spring Harbor Press, Cold Spring Harbor, N. Y., 1988; Ausubel et al., In: *Current Protocols in Molecular Biology*, John, Wiley & Sons, Inc., NY, 1994, etc.).

In the present disclosure, the term "expression vector" refers to a vector containing a nucleotide sequence encoding at least a part of a transcribed gene product. In some cases, the RNA molecule is post-translated into a protein, a polypeptide or a peptide. The expression vector may contain various regulatory sequences. A vector or an expression vector may further contain a nucleotide sequence providing another function, in addition to a regulatory sequence regulating transcription and translation.

In the present disclosure, the term "host cell" refers to a cell of any transformable organism, including a eukaryote and a prokaryote, which is capable of replicating the vector or expressing a gene encoded by the vector. The host cell may be transfected or transformed by the vector, which means a process by which an exogenous nucleotide molecule is delivered or introduced into the host cell.

In a specific exemplary embodiment of the present disclosure, the host cell of the present disclosure is a bacterial cell, more specifically a Gram-negative bacterial cell. The cell is adequate for the present disclosure in that it has a periplasmic region the inner and outer membranes. Specific examples of the host cell according to the present disclosure include the cell of *E. coli, Pseudomonas aeruginosa, Vibrio cholera, Salmonella typhimurium, Shigella flexneri, Haemophilus influenza, Bordotella pertussi, Erwinia amylovora, Rhizobium* sp., etc., although not being limited thereto.

In the preparation method according to the present disclosure, the purification of the antibody may include filtration, anion-exchange or cation-exchange chromatography, high-performance liquid chromatography (HPLC), affinity chromatography or a combination thereof. Specifically, affinity chromatography using protein A may be used.

In another aspect, the present disclosure provides a method for screening a polypeptide containing an Fc domain binding to FcγRIIIa, which includes:

a) a step of establishing a library of a polypeptide containing an Fc domain including 8 amino acid substitutions (S298G, T299A, K326I, A327Y, L328G, E382V, N390D and M428L) to which a random point mutation has been introduced; and b) a step of screening a polypeptide containing an Fc domain binding to FcγRIIIa from the library.

The substituted Fc domain of the present disclosure may further include an amino acid substitution in addition to the 8 amino acid substitutions.

In a specific exemplary embodiment of the present disclosure, the present disclosure relates to a method for screening a polypeptide containing an Fc domain binding to FcγRIIIa, which includes:

a) a step of establishing a library of a polypeptide containing an Fc domain including 8 amino acid substitutions of S298G, T299A, K326I, A327Y, L328G, E382V, N390D and M428L according to the Kabat numbering system to which a random point mutation has been introduced additionally; and b) a step of screening a polypeptide containing an Fc domain with improved binding ability for FcγRIIIa from the library as compared to the Fc domain with only the 8 amino acids substituted.

In the examples of the present disclosure, an Fc library was established using a bacterial cell (specifically, *E. coli*) and variants showing high affinity for FcγRIIIa were screened therefrom (Examples 5 and 6).

The additional amino acid substitution of the Fc domain is not particularly limited. It includes specifically one or more additional amino acid substitution selected from a group consisting of amino acids 226, 243, 246, 250, 253, 264, 307, 347, 350, 400 and 421 according to the Kabat numbering system, more specifically one or more additional amino acid substitution selected from a group consisting of C226R, F243L, K246E, T250I, I253N, V264E, T307S, C347R, T350A, S400T and N421S.

The screening method according to the present disclosure may employ fluorescence-activated cell sorting (FACS) screening or other automated flow cytometry techniques. The instruments for carrying out flow cytometry are known to those skilled in the art. Examples of the instruments include FACSAria, FACS Star Plus, FACScan and FACSort (Becton Dickinson, Foster City, Calif.), Epics C (Coulter Epics Division, Hialeah, Fla.), MOFLO (Cytomation, Colorado Springs, Colo.), and MOFLO-XDP (Beckman Coulter, Indianapolis, Ind.). Generally, the flow cytometry technique involves separation of cells or other particles from a liquid sample. Typically, the purpose of flow cytometry is analyze the separated particles for one or more characteristics (for example, the presence of a labeled ligand or other molecules). The particles are sorted based on their size, refraction, light scattering, opacity, roughness, shape, fluorescence, etc. by a sensor as they flow one by one.

In another aspect, the present disclosure provides a composition containing a polypeptide containing an Fc domain including the amino acid substitution described above, a nucleotide molecule encoding the same, a vector containing the same, or an aglycosylated antibody containing the polypeptide.

In a specific exemplary embodiment of the present disclosure, the composition of the present disclosure is a pharmaceutical composition for preventing or treating cancer.

The pharmaceutical composition of the present disclosure may contain: (a) the polypeptide, aglycosylated antibody, nucleotide molecule or vector; and (b) a pharmaceutically acceptable carrier.

In another aspect, the present disclosure provides a method for preventing or treating cancer, which includes a step of administering a pharmaceutically effective amount of the polypeptide, aglycosylated antibody, nucleotide molecule or vector to a subject.

In another aspect, the present disclosure provides a use of a pharmaceutical composition for preventing or treating cancer, which contains a polypeptide containing an Fc domain including the amino acid substitution described above, a nucleotide molecule encoding the same, a vector the containing, or an aglycosylated antibody containing the polypeptide.

The pharmaceutical composition of the present disclosure may contain: (a) the polypeptide, aglycosylated antibody, nucleotide molecule or vector; and (b) a pharmaceutically acceptable carrier.

The cancer to be prepared or treated in the present disclosure is not limited and includes lymphomas such as leukemia, acute lymphocytic leukemia, acute nonlymphocytic leukemia, chronic lymphocytic leukemia, chronic myelogenous leukemia, Hodgkin's disease, non-Hodgkin lymphoma, multiple myeloma, etc., childhood solid tumors such as brain tumor, neuroblastoma, retinoblastoma, Wilms' tumor, bone tumor, soft-tissue sarcoma, etc., and common adult solid tumors such as lung cancer, breast cancer, prostate cancer, urinary cancer, uterine cancer, oral cancer, pancreatic cancer, melanoma and other skin cancers, stomach cancer, ovarian cancer, brain tumor, liver cancer, laryngeal cancer, thyroid cancer, esophageal cancer, testicular cancer, etc.

The pharmaceutically acceptable carrier contained in the pharmaceutical composition of the present disclosure is one commonly used for preparation and includes lactose, dextrose, sucrose, sorbitol, mannitol, starch, acacia gum, calcium phosphate, alginate, gelatin, calcium silicate, microcrystalline cellulose, polyvinylpyrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further contain a lubricant, a humectant, a sweetener, a flavorant, an emulsifier, a suspending agent, a preservative, etc. in addition to the above-described ingredients. Adequate pharmaceutically acceptable carriers and preparations are described in detail in Remington's Pharmaceutical Sciences (19th ed., 1995).

The pharmaceutical composition of the present disclosure may be administered orally or parenterally, specifically parenterally. For example, it may be administered via intravenous injection, topical injection, intraperitoneal injection, etc.

An adequate administration dosage of the pharmaceutical composition of the present disclosure varies depending on factors such as formulation method, administration method, the age, body weight, sex and pathological condition of a patient, diet, administration time, administration route, excretion rate and response sensitivity. A normally skilled practitioner can easily determine and prescribe an administration dosage effective for desired treatment or prevention. In a specific exemplary embodiment of the present disclosure, a daily administration dosage of the pharmaceutical composition of the present disclosure is 0.0001-100 mg/kg.

The pharmaceutical composition of the present disclosure may be prepared as a formulation for single-dose or multiple-dose formulation using a pharmaceutically acceptable carrier and/or excipient according to a method that can be easily carried out by those of ordinary skill in the art to which the present disclosure belongs. The formulation may be in the form of a solution in an oily or aqueous medium, a suspension, an emulsion, an extract, a powder, a granule, a tablet or a capsule, and may further contain a dispersant or a stabilizer.

The pharmaceutical composition of the present disclosure may be used either alone or in combination with common chemotherapy or radiation therapy. The combined therapy may be more effective in treating cancer. A chemotherapeutic agent that may be used together with the composition of the present disclosure includes cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicamycin, mitomycin, etoposide, tamoxifen, taxol, transplatinum, 5-fluorouracil, vincristin, vinblastine, methotrexate, etc. The radiation therapy that may be used together with the composition of the present disclosure includes X-ray radiation, γ-ray radiation, etc.

Advantageous Effects

The features and advantages of the present disclosure may be summarized as follows:

(i) The present disclosure provides a polypeptide containing an Fc domain in which a part of an amino acid sequence of a human antibody Fc domain is substituted with another amino acid sequence, or an aglycosylated antibody containing the same.

(ii) The present disclosure also provides a method for preparing the polypeptide or the aglycosylated antibody.

(iii) The Fc domain of the present disclosure has superior binding ability to FcγRIIIa selectively among Fc receptors through optimization by substituting a part of an amino acid sequence of a wild-type Fc domain with another amino acid sequence and is useful for treatment of cancer. It can be prepared as a homogeneous aglycosylated antibody through bacterial culture.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

EXAMPLES

Example 1

Fc Variant Cloning for Displaying Aglycosylated Antibody on Bacterial Inner Membrane as Full-Length IgG (A/IYG, Fc1004-IYG)

In order to display the A/IYG (U.S. Pat. No. 8,815,237) variant and Fc1004-IYG as full-length IgG, each Fc variant was constructed as a heavy chain-type plasmid. A pMopac12-PeIB-VH-CH1-CH2-CH3(wild type)-FLAG plasmid was split into two fragments for T299A substitution, and each strand was amplified with the Vent polymerase (New England Biolabs) using MJ#36, MJ#43/MJ#42 and MJ#37 primers. The two fragments were constructed into a pMopac12-PeIB-VH-CH1-CH2-CH3(T299A)-FLAG plasmid through assembly PCR using MJ#36 and MJ#37 primers, SfiI (New England Biolabs) cutting and ligation using T4 DNA ligase (Invitrogen). 326I YG substitution was conducted using the plasmid as a template and using MJ#36, MJ#39/MJ#38 and MJ#37 primers by the same method (construction of pMopac12-PeIB-VH-CH1-CH2-CH3(A/IYG)-FLAG). Then, pMopac12-PeIB-VH-CH1-CH2-CH3 (Fc1004-IYG)-FLAG was conducted by introducing 326I YG point mutation to pMopac12-PeIB-VH-CH1-CH2-CH3 (Fc1004)-FLAG using the same MJ#36, MJ#39/MJ#38 and MJ#37 primers.

TABLE 1

Primers used in the experiment

| Primer # | | Nucleotide sequence (5'→3') |
|---|---|---|
| MJ#36 | (SEQ ID NO 17) | CGCAGCGAGGCCCAGCCGGCCATGGCGGA GGTTCAATTAGTGGAATCTG |
| MJ#43 | (SEQ ID NO 18) | GGACGCTGACCACACGGTACGCGCTGTTG TACTGCTCCTCCG |
| MJ#42 | (SEQ ID NO 19) | CGGGAGGAGCAGTACAACAGCGCGTACCG TGTGGTCAGCGTCC |
| MJ#37 | (SEQ ID NO 20) | CGCAATTCGGCCCCCGAGGCCCCTTTACC CGGGGACAGGGAG |
| MJ#39 | (SEQ ID NO 21) | GGTTTTCTCGATGGGGGCTGGGCCATAAA TGTTGGAGACCTTGCATTTGTACTCCTTG |
| MJ#38 | (SEQ ID NO 22) | CAAGGAGTACAAATGCAAGGTCTCCAACA TTTATGGCCCAGCCCCCATCGAGAAACC |
| MJ#45 | (SEQ ID NO 23) | CGACAAGAAAGTTGAGCCCAAATCTTGT |
| MJ#46 | (SEQ ID NO 24) | CGCAATTCCGGCCCCCGAGGCCCC |
| MJ#44 | (SEQ ID NO 25) | ACAAGATTTGGGCTCAACTTTCTTGTCG |
| MJ#2 | (SEQ ID NO 26) | CTGCCCATGTTGACGATTG |
| MJ#49 | (SEQ ID NO 27) | CGCAGCGAGCGCGCACTCCATGGCGGAGG TTCAATTAGTGGAATCTG |
| MJ#50 | (SEQ ID NO 28) | CCCTAAAATCTAGACCTTTACCCGGGGAC AGGGAG |

Example 2

Figure 1:
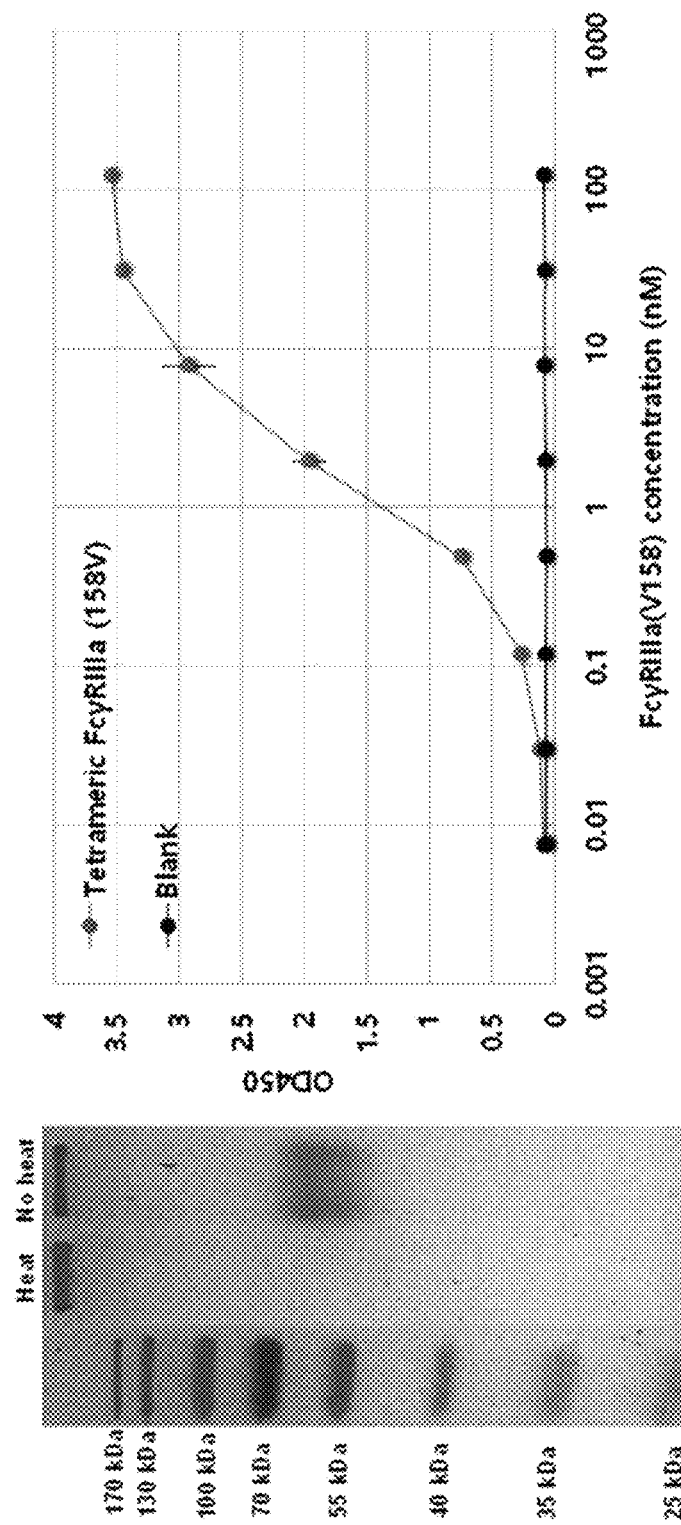
FIG. 1 shows an image of purified tetrameric FcγRIIIa (left, SDS-PAGE) and an ELISA result (right) for investigating its activity.
Figure 2:
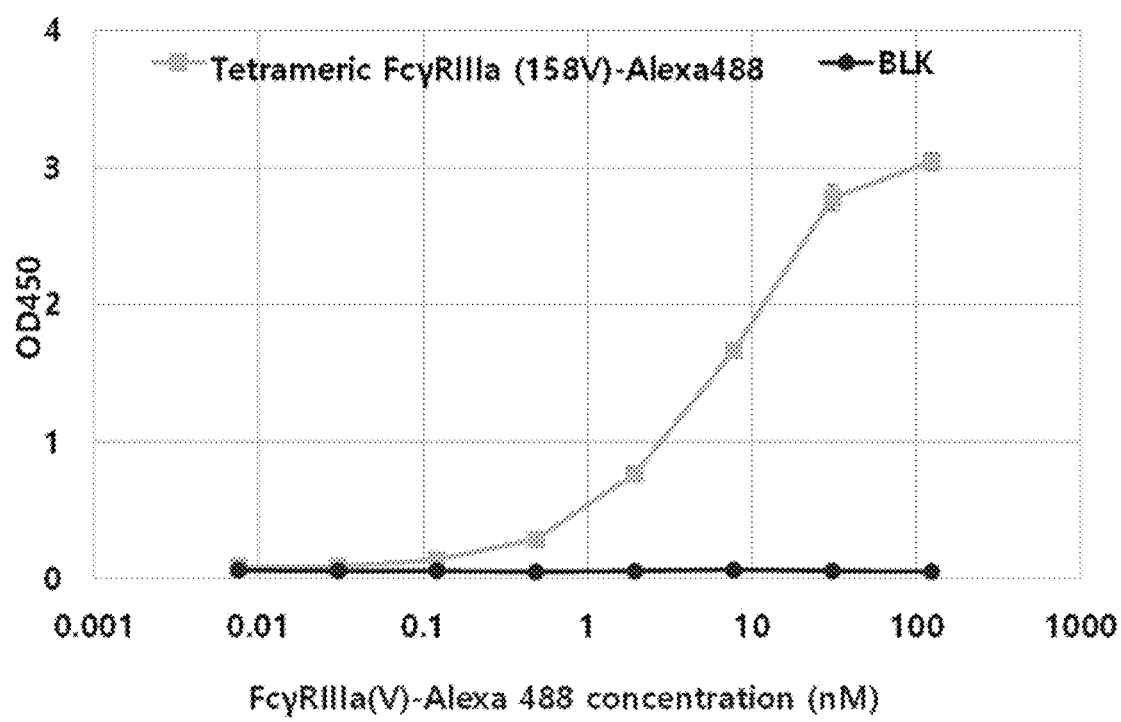
FIG. 2 shows an ELISA result for investigating the activity of tetrameric FcγRIIIa fluorescence-labeled with Alexa 488 Flour.

Preparation of Tetrameric FcγRIIIa and Fluorescence Labeling Using Alexa 488 Fluor The pMAZ-FcγRIIIa (V158)-FLAG-streptavidin-His plasmid was expressed in 300 mL of HEK 293F cells and affinity chromatography was conducted using 1 mL of Ni-NTA agarose (Qiagen) slurry. After the culturing, the suspended culture was centrifuged at 7000 rpm for 10 minutes to remove the cells. The supernatant was equilibrated using 25×PBS and then filtered through a 0.2-μm bottle top filter (Merck Millipore). After adding Ni-NTA slurry equilibrated with PBS and stirring at 4° C. for 16 hours, the solution was flown through a polypropylene column (Thermo Fisher Scientific). After taking the pass-through solution and binding again to a resin, it was sequentially washed with 50 mL of 1×PBS, 25 mL of 10 mM of imidazole buffer, 25 mL of 20 mM imidazole buffer and 200 μL of 250 mM imidazole buffer. After eluting with 2.5 mL of 250 mM imidazole buffer and replacing the buffer with PBS through Amicon Ultra-4 (Merck Millipore), the purified protein was investigated by SDS-PAGE (FIG. 1). The activity of the purified protein was investigated by analyzing binding to Rituxan (Roche) by ELISA, and 1 mg was taken and fluorescence-labeled using the Alexa Fluor 488 protein labeling kit (Thermo Fisher Scientific). After the fluorescence labeling, the activity was analyzed by ELISA (FIG. 2). Through this, high-purity active tetrameric FcγRIIIa was prepared successfully, and the activity of the protein was maintained even after the fluorescence labeling with Alexa 488 Flour.

Example 3

Comparison of Binding Ability of Wild Type, Fc1004 and A/IYG for FcγRIIIa

Figure 3:
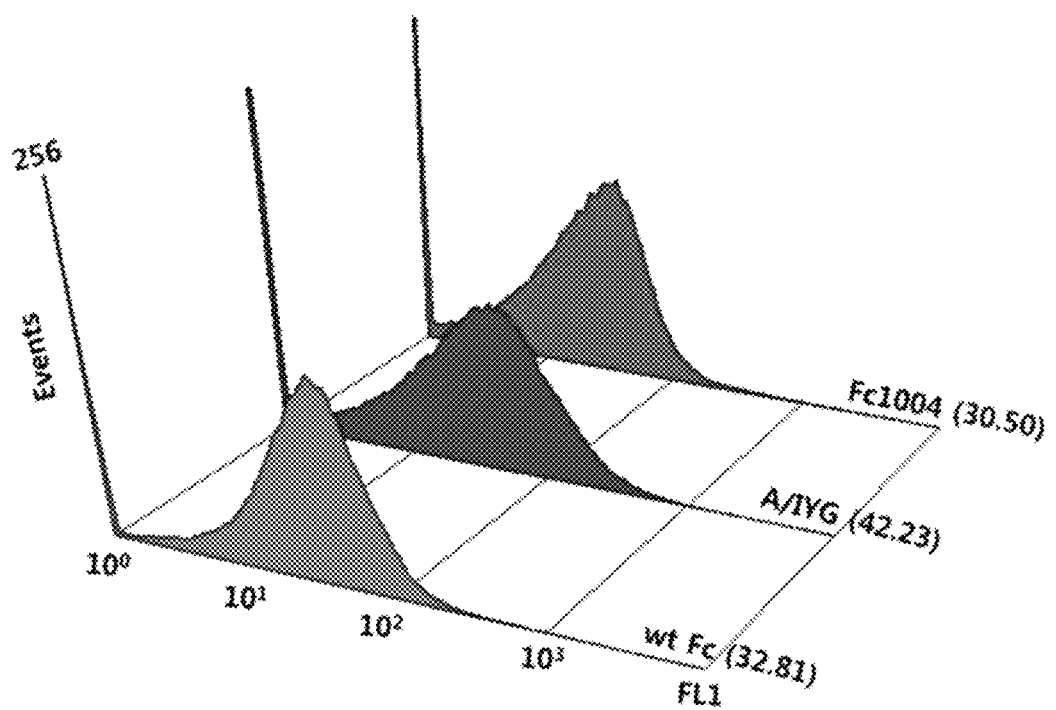
FIG. 3 compares the binding ability of A/IYG and Fc1004 for FcγRIIIa.

Because the clones to be analyzed are heavy chain-encoding plasmids, pMopac12-PeIB-VH-CH1-CH2-CH3 (wild type)-FLAG, pMopac12-PeIB-VH-CH1-CH2-CH3 (Fc1004)-FLAG and pMopac12-PeIB-VH-CH1-CH2-CH3 (A/IYG)-FLAG, E. coli Jude 1 cells (F' [Tn10(Tet$^r$) proAB$^+$ lacI$^q$Δ(lacZ)M15] mcrA Δ(mrr-hsdRMS-mcrBC) 80dlacZΔM15 ΔlacX74 deoR recA1 araD139 Δ(ara leu) 7697 galU galKrpsLendA1nupG) (Kawarasaki et al., 2003) were transformed with the pBAD30-Km-PelB-VL-Ck-NlpA-VL-Ck-His-cMyc plasmid, such that heavy chains and light chains could be expressed in the periplasmic region. After culturing in 5 mL of Terrific broth (TB, BD) containing 2% glucose (Sigma-Aldrich) at 37° C. for 16 hours, 5.5 mL of TB was transferred to a 100-mL flask for 1:100 inoculation. After culturing to OD$_{600}$=0.6, followed by cooling at 25° C. and 250 rpm for 20 minutes, overexpression was conducted at 25° C. and 250 rpm for 20 hours by adding 0.2% arabinose and 1 mM IPTG. After the overexpression, the cells were OD$_{600}$ normalized and harvested by centrifuging at 14000 rpm for 1 minute. A washing procedure of resuspending the cells by adding 1 mL of 10 mM Tris-HCl (pH 8.0) and centrifuging for 1 minute was repeated twice. After resuspending the cells in 1 mL of STE [0.5 M sucrose, 10 mM Tris-HCl, 10 mM EDTA (pH 8.0)], the outer membrane of the cells was removed by rotating at 37° C. for 30 minutes. After centrifuging, discarding the supernatant and resuspending by adding 1 mL of solution A [0.5 M sucrose, 20 mM MgCl$_2$, 10 mM MOPS pH 6.8], centrifugation was carried out. After resuspending in 1 mL of a solution obtained by mixing 1 mL of solution A and 20 μL of 50 mg/mL lysozyme solution, the peptidoglycan layer was removed by rotating at 37° C. for 15 minutes. After centrifuging, removing the supernatant and resuspending in 1 mL of PBS, 300 μL was taken and spheroplasts were fluorescence-labeled by rotating at room temperature after adding 700 μL of PBS and fluorescence-labeled tetrameric FcγRIIIa-Alexa 488 Flour. After the labeling and washing once with 1 mL of PBS, analysis was conducted using the Guava instrument (Merck Millipore) (FIG. 3). As a result, all of the wild-type Fc, A/IYG and Fc1004 showed mean values of 30-42, suggesting that binding to FcγRIIIa does not occur well.

Example 4

Figure 4:
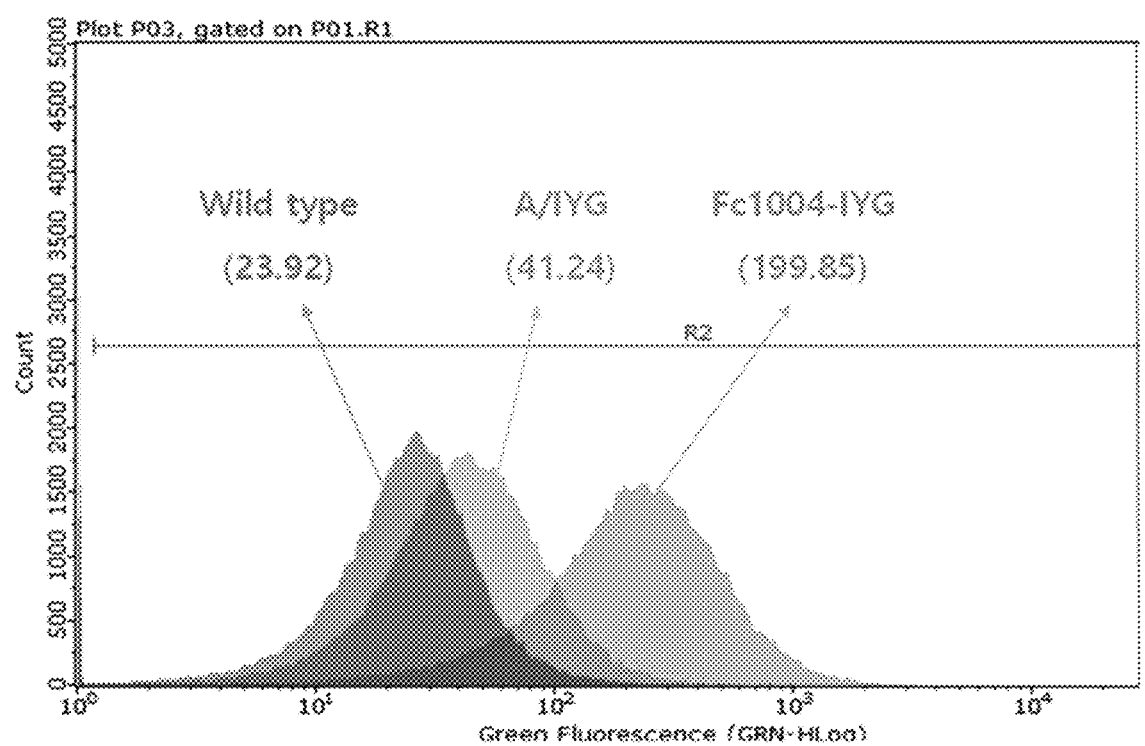
FIG. 4 compares the binding ability of A/IYG and Fc1004-IYG for FcγRIIIa.

Comparison of Binding Ability of A/IYG and Fc1004-IYG for FcγRIIIa pMopac12-PelB-VH-CH1-CH2-CH3 (IYG)-FLAG and pMopac12-PelB-VH-CH1-CH2-CH3 (Fc1004-IYG)-FLAG were prepared such that heavy chains and light chains could be expressed in the periplasmic region by transforming E. coli Jude 1 cells together with the pBAD30-Km-PelB-VL-Ck-NlpA-VL-Ck-His-cMyc plasmid. After culturing the cells at 37° C. for 16 hours in 5 mL of TB containing 2% glucose, 5.5 mL of TB was transferred to a 100-mL flask for 1:100 inoculation. After culturing to $OD_{600}$=0.6, followed by cooling at 25° C. and 250 rpm for 20 minutes, overexpression was conducted at 25° C. and 250 rpm for 20 hours by adding 0.2% arabinose and 1 mM IPTG. After the overexpression, the cells were $OD_{600}$ normalized and harvested by centrifuging at 14000 rpm for 1 minute. A washing procedure of resuspending the cells by adding 1 mL of 10 mM Tris-HCl (pH 8.0) and centrifuging for 1 minute was repeated twice. After resuspending the cells in 1 mL of STE [0.5 M sucrose, 10 mM Tris-HCl, 10 mM EDTA (pH 8.0)], the outer membrane of the cells was removed by rotating at 37° C. for 30 minutes. After centrifuging, discarding the supernatant and resuspending by adding 1 mL of solution A [0.5 M sucrose, 20 mM $MgCl_2$, 10 mM MOPS pH 6.8], centrifugation was carried out. After resuspending in 1 mL of a solution obtained by mixing 1 mL of solution A and 20 μL of 50 mg/mL lysozyme solution, the peptidoglycan layer was removed by rotating at 37° C. for 15 minutes. After centrifuging, removing the supernatant and resuspending in 1 mL of PBS, 300 μL was taken and spheroplasts were fluorescence-labeled by rotating at room temperature after adding 700 μL of PBS and fluorescence-labeled tetrameric FcγRIIIa-Alexa 488 Flour. After the labeling and washing once with 1 mL of PBS, analysis was conducted using the Guava instrument (Merck Millipore) (FIG. 4). As a result, the fluorescence signal intensity of Fc1004-IYG was 199.85, which is 8.4 times of wild type (23.92). Accordingly, it was confirmed that the binding ability of Fc1004-IYG was significantly improved as compared to A/IYG (41.24, 1.7 times of wild type), which is known to exhibit the highest affinity for FcγRIIIa among the currently known aglycosylated antibody Fc variants.

Example 5

Construction of Aglycosylated Antibody Library Based on Fc1004-IYG

Figure 5:
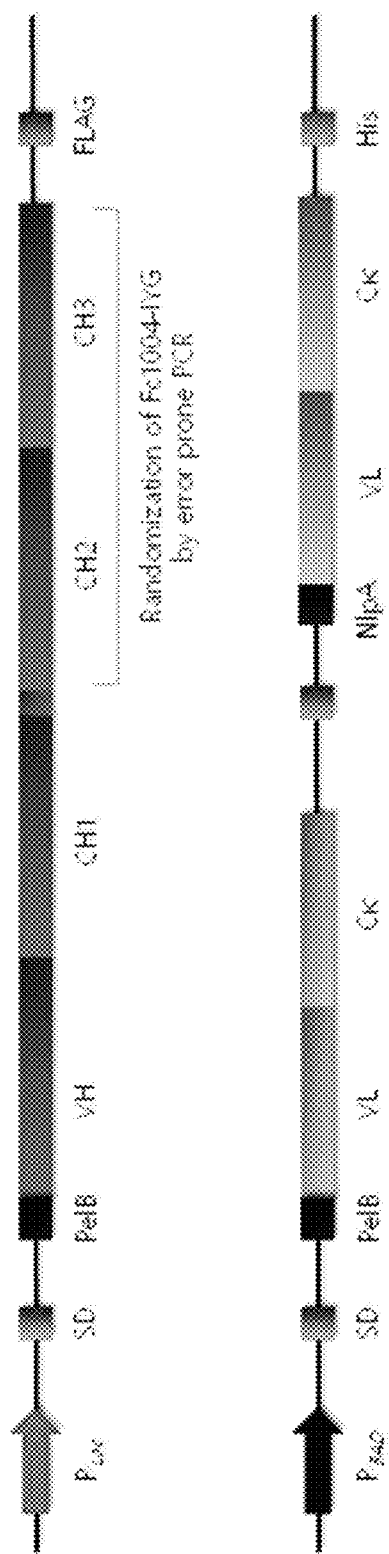
FIG. 5 schematically shows the establishment of an aglycosylated antibody Fc library based on Fc1004-IYG.

In order to construct an aglycosylated antibody Fc library based on Fc1004-IYG, error prone PCR and assembly PCR were conducted using pMopac12-PelB-VH-CH1-CH2-CH3 (Fc1004-IYG)-FLAG as a template. The error prone PCR technique using Taq polymerase (Invitrogen) was used to introduce random point mutation to the Fc (CH2-CH3) region. The point mutation was introduced to 0.5% of nucleotides of the full-length Fc gene using MJ#45 and MJ#46 primers. The forward region of Fc was designed to overlap with Fab, such that assembly as heavy chains was possible. The entire heavy chain-type PCR product was constructed by conducting conventional PCR for the Fab (VH-CH1) region using MJ#36 and MJ#44 primers and Vent polymerase, and then conducting assembly PCR to ligate the Fab fragment with the Fc fragment using MJ#36 and MJ#46 primers. Then, after SfiI restriction enzyme treatment and ligation, the heavy chain-type aglycosylated antibody Fc library was constructed by transforming into Jude 1 cells (library size: 1.14×10$^9$, experimental error rate: 0.457%). After obtaining the gene from the library and then transforming again to Jude 1 cells transformed with pBAD30-Km-PelB-VL-Ck-NlpA-VL-Ck-His-cMyc, a library in which the full-length IgG was displayed on the inner membrane of E. coli was constructed (FIG. 5).

Example 6

Screening of Constructed Library by Flow Cytometry and Selection of Variants MG42, MG48, MG59, MG87, etc. (Confirmation of Binding Ability for FcγRIIIa)

Figure 6A:
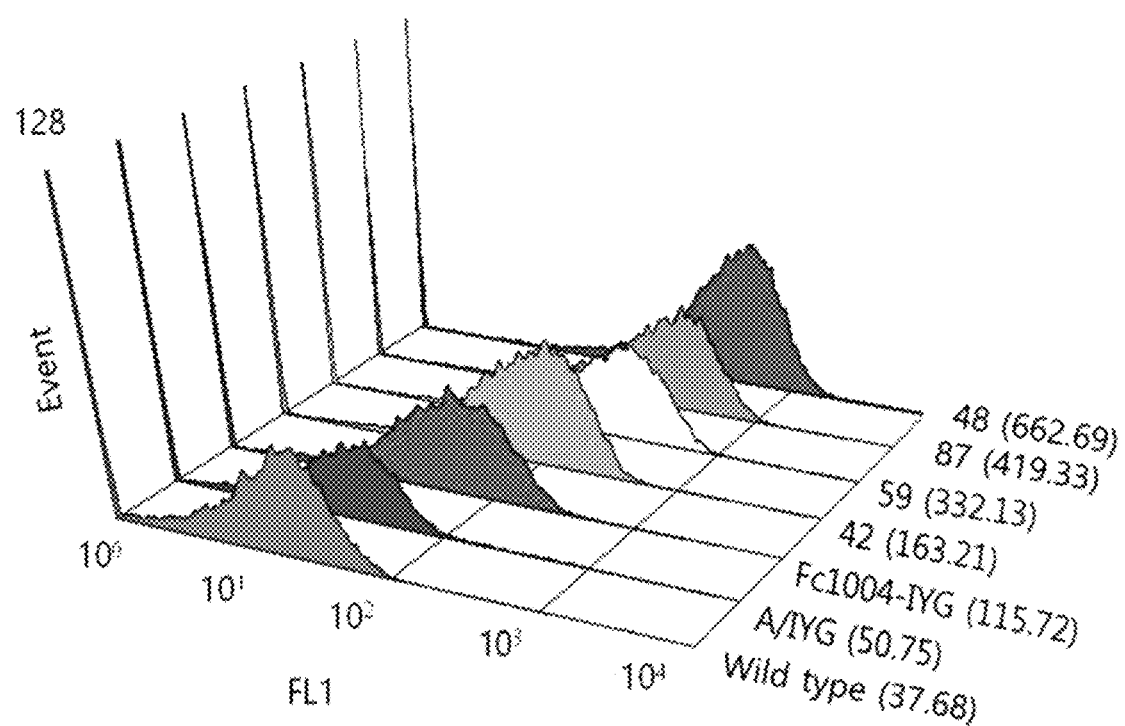
FIGS. 6A-6C compare the binding ability of FcγRIIIa high-affinity Fc variants screened through library screening using a flow cytometer (a and b: comparison of wild type, A/IYG, Fc1004-IYG, MG42, MG59, MG87 and MG48; c: comparison of wild type, A/IYG, Fc1004-IYG, MG61, MG86, MG54 and MG14).
Figure 6B:
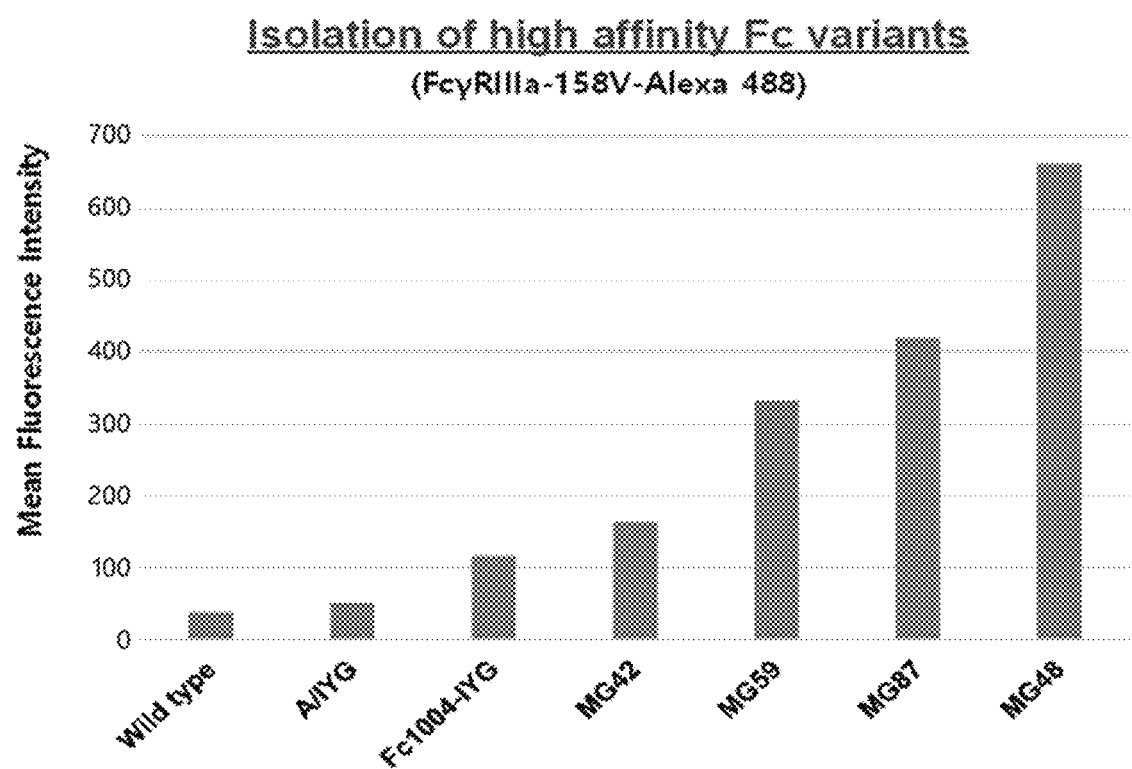

The constructed library was unfolded in 25 mL of TB containing 2% glucose in a 250-mL flask, incubated in a vial (1 mL) at 37° C. for 4 hours, and then transferred to 110 mL of TB in a 2.5-L flask for 1:100 inoculation. After culturing to $OD_{600}$=0.6, followed by cooling at 25° C. and 250 rpm for 20 minutes, overexpression was conducted at 25° C. and 250 rpm for 20 hours by adding 0.2% arabinose and 1 mM IPTG. After the overexpression, the cells were $OD_{600}$ normalized and harvested by centrifuging at 14000 rpm for 1 minute. After preparing spheroplasts as described above, the cells were labeled with tetrameric FcγRIIIa-Alexa 488 Flour and then washed once with 1 mL of PBS. Finally, the sample resuspended in 1 mL of PBS was diluted with 20 mL of PBS and only the cells emitting upper 3% signals were sorted using the S3 cell sorter (BioRad). The separated cells were sorted once again. Genes were amplified from the sorted cells by PCR using MJ#36 and MJ#2 primers and Taq polymerase (Biosesang). Then, a sublibrary in which the genes of the sorted cells were amplified was obtained through SfiI restriction enzyme treatment, ligation and transformation. After repeating this procedure for a total of 5 rounds, variants exhibiting high affinity for FcγRIIIa were selected by analyzing more than 90 individual clones (FIGS. 6A and 6B, Table 2, position of mutation follows the Kabat EU numbering system (Kabat et al., "Sequences of Proteins of Immunological Interest", 5th Ed., U.S. Department of Health and Human Services, NIH Publication No. 91-3242, 1991).

TABLE 2

Point mutation of major variants

| $F_C$ variants | Point mutation |
| --- | --- |
| A/IYG (SEQ ID NO 5) | T299A, K326I, A327Y, L328G |
| Fc1004 (SEQ ID NO 3) | 5298G, T299A, E382V, N390D, M428L |
| Fc1004-IYG (SEQ ID NO 7) | 5298G, T299A, K326I, A327Y, L328G, E382V, N390D, M428L |
| MG42 (SEQ ID NO 9) | (Fc1004-IYG)+264E, 350A, 421S |
| MG48 (SEQ ID NO 11) | (Fc1004-IYG)+264E, 350A |
| MG59 (SEQ ID NO 13) | (Fc1004-IYG)+264E |
| MG87 (SEQ ID NO 15) | (Fc1004-IYG)+264E, 421S |

Figure 6C:
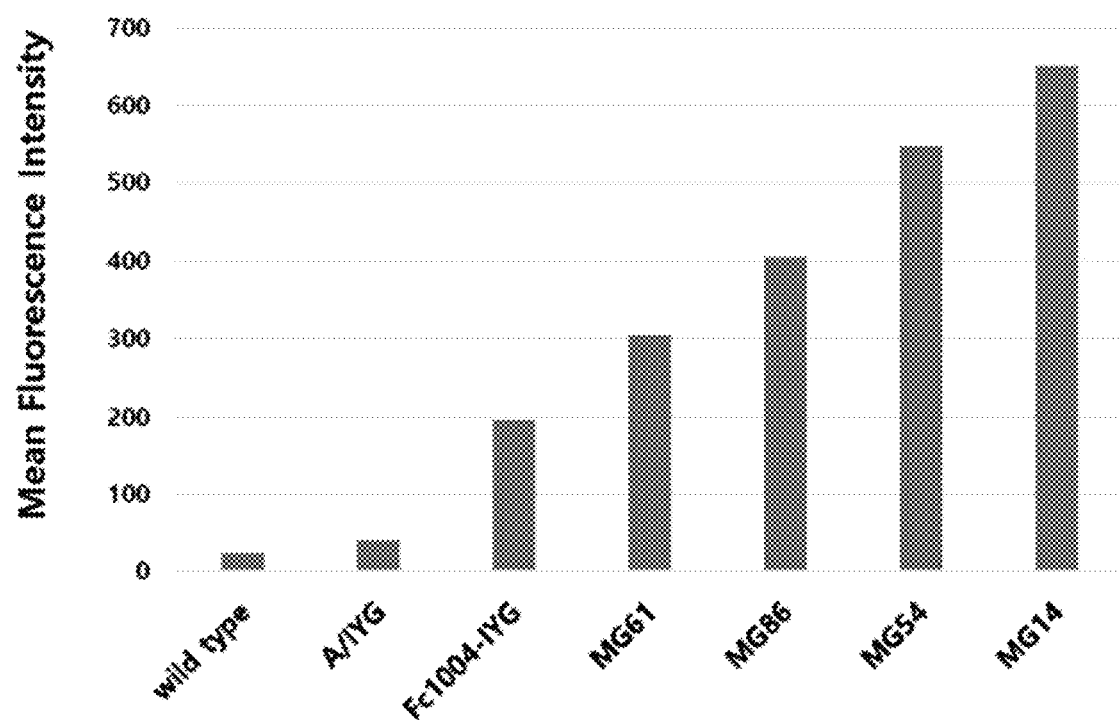

In addition to these variants, the variants exhibiting higher affinity for FcγRIIIa than A/IYG were screened additionally (MG61: (Fc1004-IYG)+T307S, MG86: (Fc1004-IYG)+C226R+F243L+K246E MG54: (Fc1004-IYG)+T250I+I253N, MG14: (Fc1004-IYG)+C347R) (FIG. 6C).

Example 7

Figure 7:
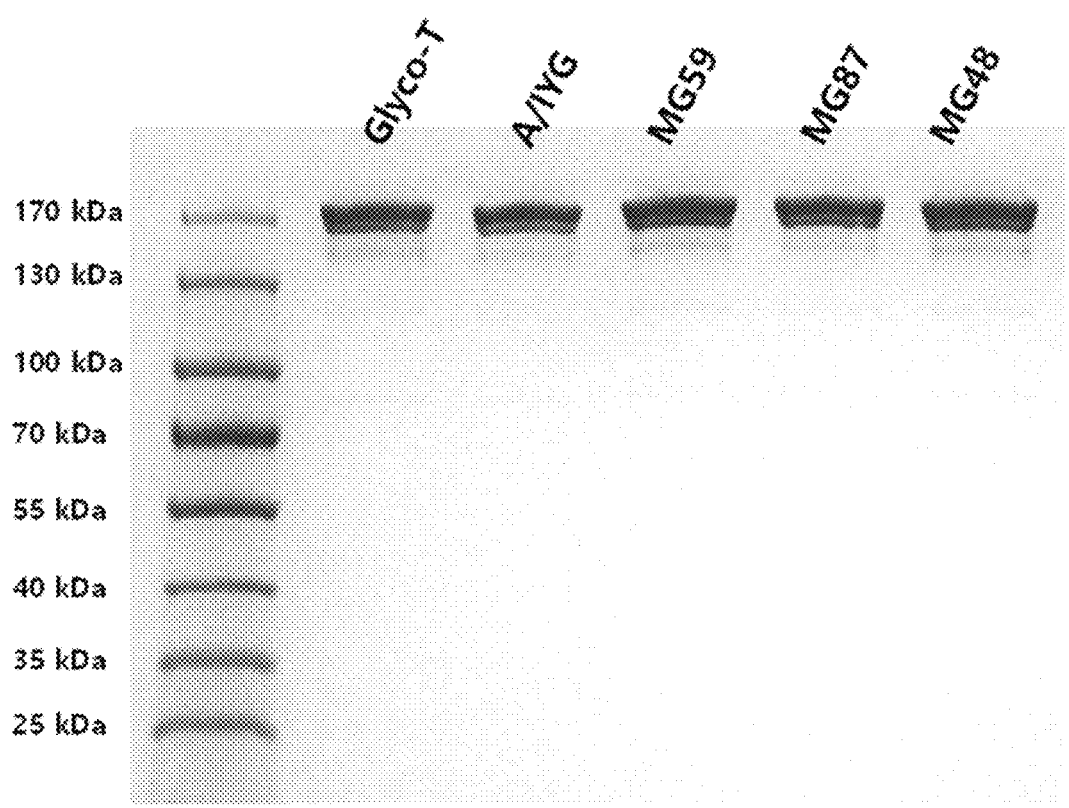
FIG. 7 shows an image showing an SDS-PAGE of purified screened variants and controls (wild type, A/IYG).

Cloning for Expression of Screened Variants in Animal Cells, and Expression and Purification Thereof In order to prepare MG59, MG87 and MG48 among the screened variants together with wild type and A/IYG, as controls, into IgG forms soluble in HEK293F cells, pMAZ-IgH (wild type), pMAZ-IgH (A/IYG), pMAZ-IgH (MG59), pMAZ-IgH (MG87) and pMAZ-IgH (MG48) were constructed by amplifying the 'VH-CH1-CH2-CH3' region encoding the heavy chain by PCR using the Vent polymerase and MJ#49 and MJ#50 primers, followed by treatment with BssHII and XbaI restriction enzymes (New England Biolabs) and ligation. For expression as IgG, they were co-transfected into HEK 293F cells together with the pMAZ-IgL plasmid and expressed transiently at 300 mL scale. After culturing and removing the medium by centrifuging at 7000 rpm for 10 minutes, the supernatant was equilibrated using 25×PBS and filtered through a 0.2-μm bottle top filter (Merck Millipore). After adding 1 mL of protein A agarose (Genscript) slurry equilibrated with PBS and stirring at 4° C. for 16 hours, the solution was flown through a polypropylene column (Thermo Fisher Scientific). After taking the pass-through solution and binding again to a resin, it was washed by flowing 10 CV (column volume) or more of 1×PBS. After eluting with 3 mL of 100 mM glycine-HCl (pH 2.7), the eluate was neutralized immediately with 1 mL of 1 M Tris (pH 8.0). After replacing the buffer with PBS through Amicon Ultra-4 (Merck Millipore), the purified protein was investigated by SDS-PAGE (BioRad) (FIG. 7). It was confirmed that the protein in the form of IgG (150 kDa) was purified with high purity on the SDS-PAGE.

Example 8

ELISA Analysis of Variants for Confirmation of Binding Ability for FcRs

Figure 8:
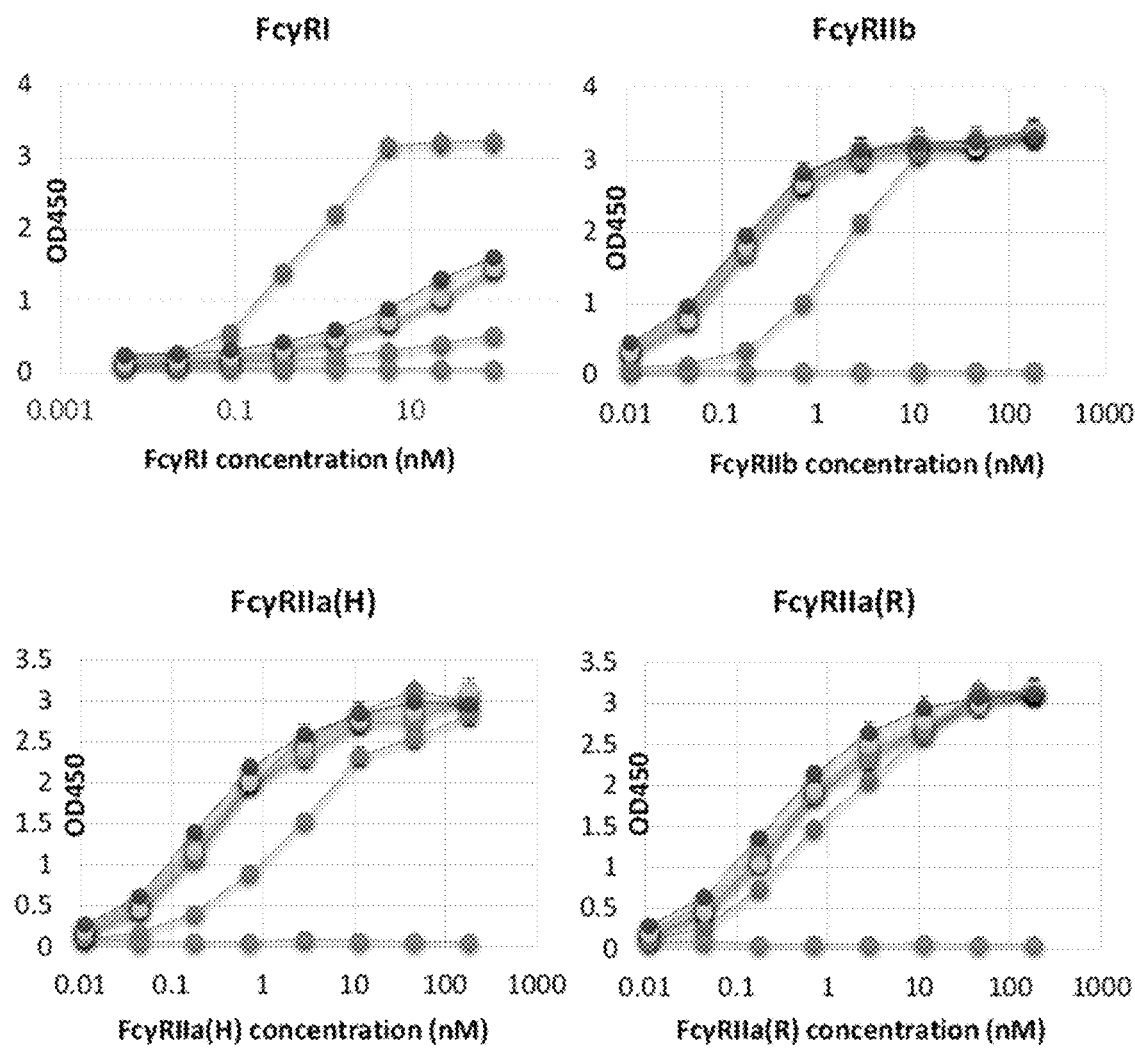
FIG. 8 shows a result of analyzing the affinity of variants for various FcγRs by ELISA.

50 μL of each IgG Fc variant diluted with 0.05 M $Na_2CO_3$ (pH 9.6) to 4 μg/mL was fixed onto the Flat Bottom Polystyrene High Bind 96-well microplate (Costar) at 4° C. for 16 hours, and then blocked at room temperature with 100 μL of 5% BSA (in 0.05% PBST) for 2 hours. After washing 4 times with 180 μL of 0.05% PBST, 50 μL of FcRs serially diluted with a blocking solution was added to each well. After the washing, antibody reaction was conducted at room temperature for 1 hour using 50 μL of anti-His-HRP conjugate (Sigma-Aldrich) and anti-GST-HRP conjugate (GE Healthcare), respectively. After adding 50 μL of 1-Step Ultra TMB-ELISA substrate solution (Thermo Fisher Scientific) for color development, the reaction was terminated by adding 50 μL of 2 M $H_2SO_4$ and analysis was conducted using the Epoch microplate spectrophotometer (BioTek) (FIG. 8). All the experiments were conducted in duplicates. The binding ability for the FcRs (FcγRI, FcγRIIa(H), FcγRIIa(R), FcγRIIb, FcRn) was confirmed through the ELISA analysis.

Example 9

Measurement of $K_D$ Values of FcγRIIIa and Trastuzumab Variants by SPR

Figure 9A:
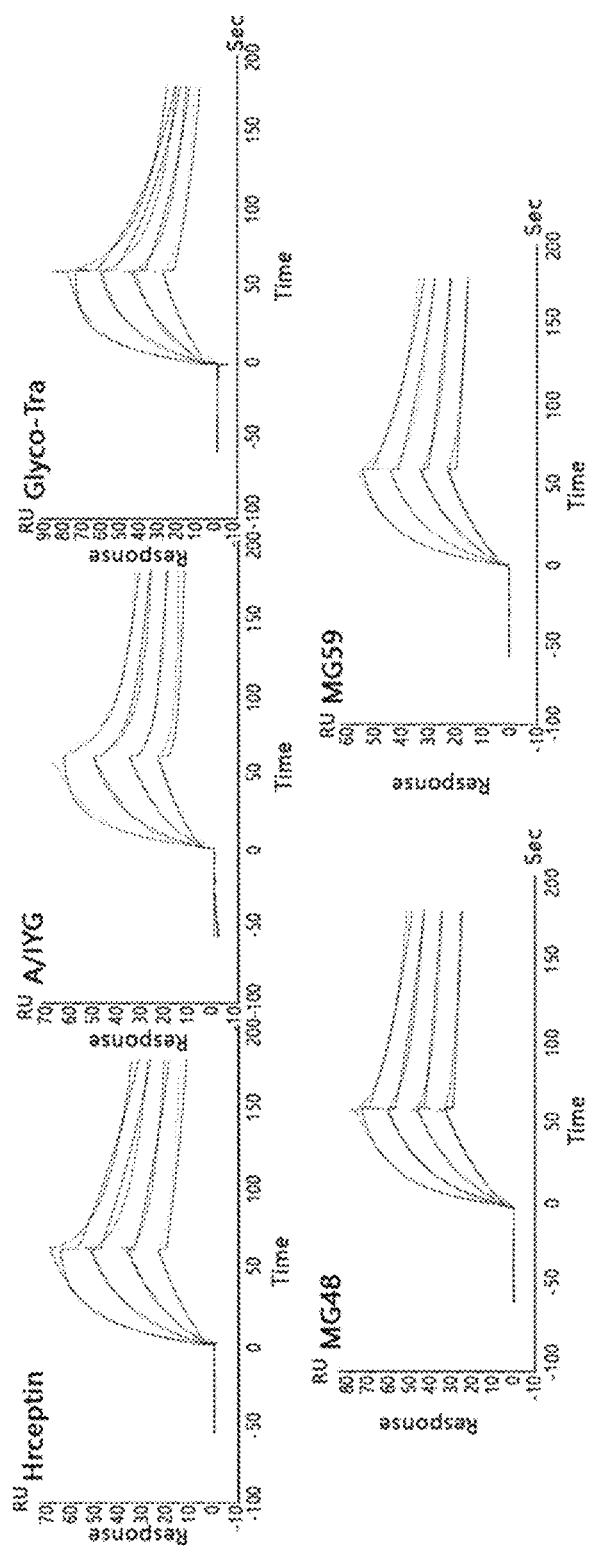
FIGS. 9A-9B show an SPR analysis result of variants (a. binding ability analysis for FcγRIIIa (V158); b. binding ability analysis for FcγRIIIa (F158)).
Figure 9B:
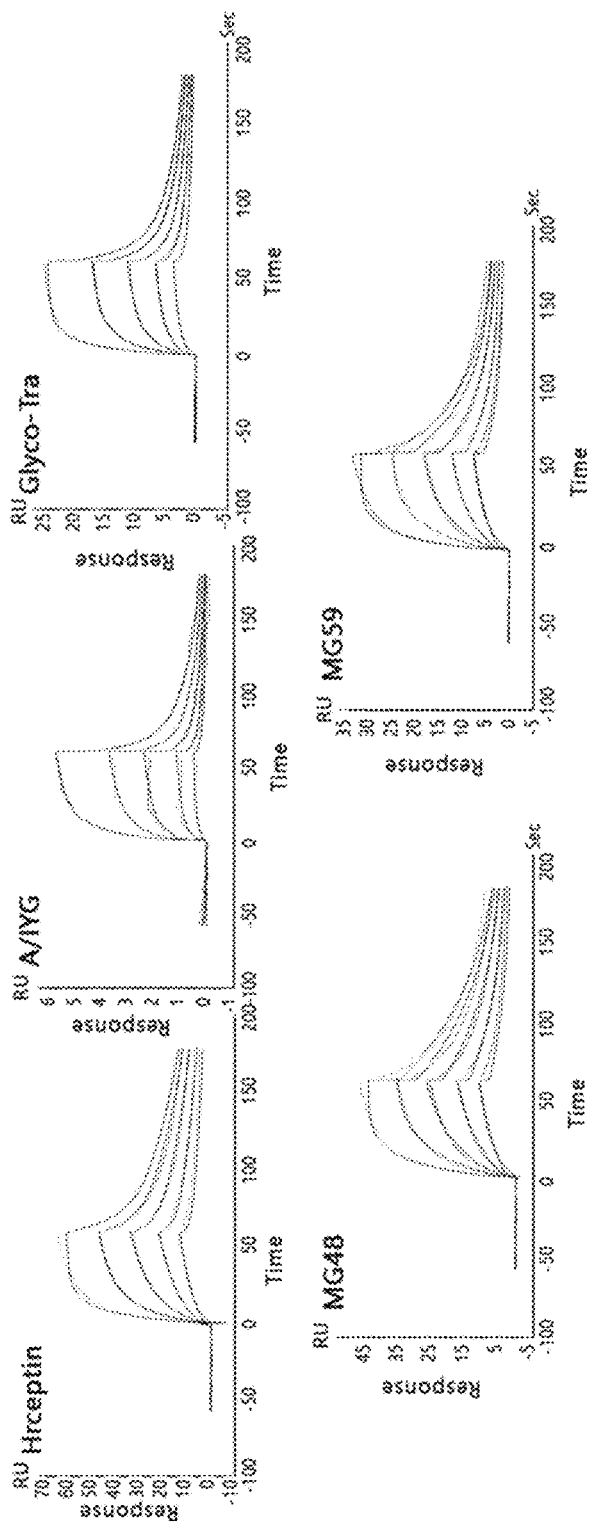

The binding ability of the trastuzumab variants was measured using BIAcore T200 (GE Healthcare). After fixing each of the wild-type aglycosylated antibody (Aglyco-T), A/IYG, wild-type glycosylated antibody (Glyco-T; produced by culturing HEK 293F cells), Herceptin (clinical drug produced in CHO cells), MG48 and MG59 on a CM5 chip through amine coupling, dimeric FcγRIIIa-V158-GST, FcγRIIa-F158-GST was injected using HBS-EP buffer (10 mM HEPES pH 7.4, 150 mM NaCl, 3.4 mM EDTA, and 0.005% P20 surfactant) (GE Healthcare) and the binding ability was analyzed (FIG. 9). The regeneration of the CM5 chip was conducted sequentially by using 50 mM glycine (pH 3.9), 50 mM glycine (pH 9.5) and 3 M NaCl. The 2:1 bivalent analyte model of the BIAevaluation 3.2 software (GE Healthcare) was used to calculate the equilibrium dissociation constants ($K_D$) of monovalent receptor binding (Table 3).

TABLE 3

SPR $K_D$ values of variants

| | $K_D$ (M) | | Fold increase |
|---|---|---|---|
| | FcγRIIIa (158V) | FcγRIIIa (158F) | (V/F) |
| Aglyco-T | N.D | N.D | 0 |
| A/IYG | $1.110 \times 10^{-6}$ | $1.737 \times 10^{-5}$ | 1 |
| Glyco-T (HEK) | $1.200 \times 10^{-7}$ | $5.782 \times 10^{-6}$ | 9.25/3.00 |
| Herceptin (CHO) | $8.418 \times 10^{-8}$ | $5.142 \times 10^{-6}$ | 13.19/3.38 |
| MG48 | $6.793 \times 10^{-8}$ | $6.763 \times 10^{-7}$ | 16.34/25.68 |
| MG59 | $1.070 \times 10^{-7}$ | $1.049 \times 10^{-6}$ | 10.37/16.56 |

As a result, it was confirmed that the MG48 and MG59 screened in the present disclosure showed binding ability improved by up to 16 times for FcγRIIIa-V158 and up to 25 times or more for FcγRIIa-F158, as compared to A/IYG.

Example 10

Investigation of HER2 Expression Level in SKBR-3 and MCF-7 Target Cells

Figure 10:
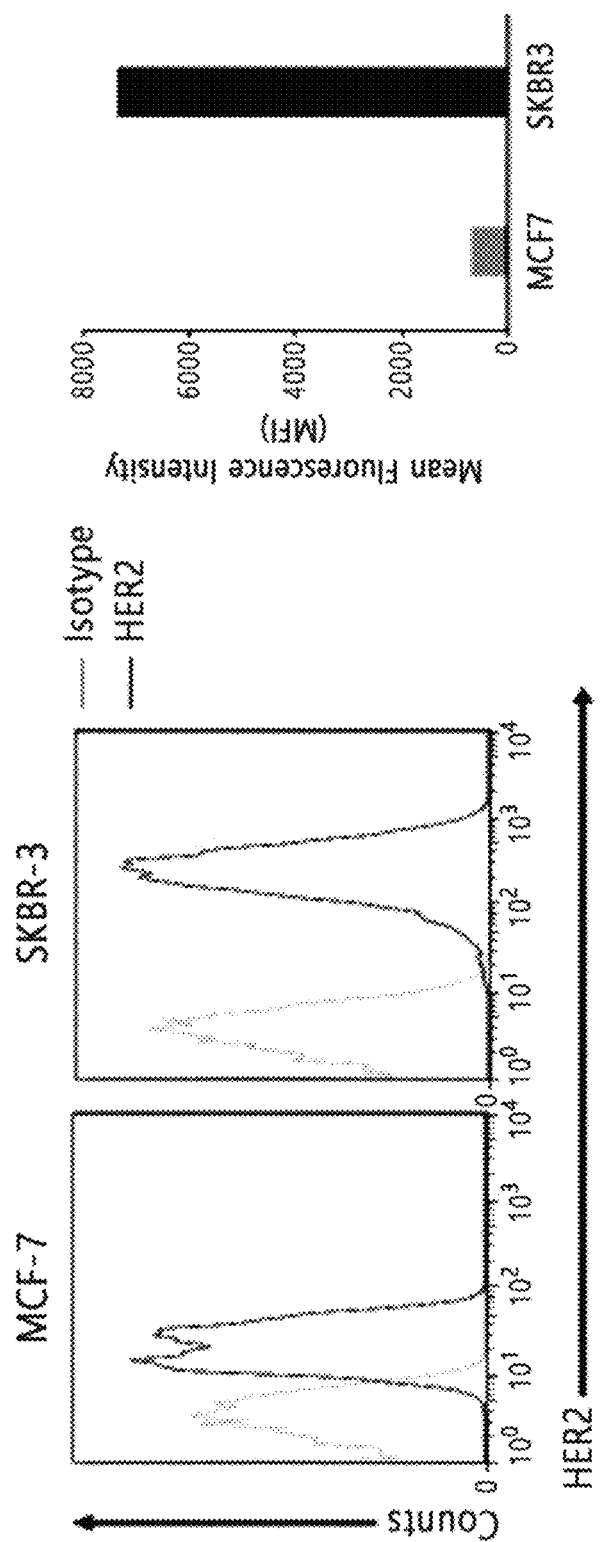
FIG. 10 shows a result of investigating the HER2 expression level of MCF-7 and SKBR-3.

Cells were cultured on a 100-mm dish (80% confluency). After removing the medium and washing once with DPBS, the cells were treated with 1.5 mL of Accutase (Merck Millipore) and incubated for 2-3 minutes in a 37° C. $CO_2$ incubator. After confirming that the cells adhered to the bottom of the dish, 6 mL of a cell culture medium was added. After taking all the solution including the cells using a 10-mL pipette, the solution was transferred to a 15-mL tube and centrifuged at 1200 rpm for 3 minutes. After completely removing the solution from the 15-mL tube and adding 5 mL of DPBS and mixing well with the cells, centrifugation was performed at 1200 rpm for 3 minutes. After removing the DPBS from the tube and adding 3 mL of washing buffer (PBS+1% BSA) and mixing well with the cells, centrifugation was performed at 1200 rpm for 3 minutes and the washing buffer was removed from the tube. After repeating the washing procedure 2 times, 1 mL of washing buffer was added finally and mixed well with the cells. FACS tubes (Falcon) were prepared for non-staining, isotype control (normal human IgG-Alexa 488) and trastuzumab-Alexa 488, respectively. The cells were counted and transferred to each tube at $1 \times 10^5$ cells/300 μL. After blocking at 4° C. for 15 minutes, centrifugation was carried out and the supernatant was removed. 100 μL of washing buffer was added to the FACS tube and mixed well with the cells. 1 μg of isotype control and trastuzumab-Alexa 488 was added except for the non-staining tube. After blocking light with aluminum foil and conducting antibody reaction at 4° C. for 30 minutes, centrifugation was carried out and the supernatant was removed. The remaining cells were washed by adding 1 mL of washing buffer. This procedure was repeated 3 times. After adding 300 μL of running buffer (PBS) to each tube and mixing well with the cells, FACS analysis was carried out. As a result, it was confirmed that SKBR-3 showed much higher HER2 expression than MCF-7 (FIG. 10). Accordingly, SKBR-3 exhibiting higher HER2 expression was confirmed as more adequate target cells than MCF-7 for the evaluation of the ADCC activity of the antibody sample.

Example 11

Preliminary Experiment for Determination of Effector Cell (PBMC):Target Cell (SKBR-3, MCF-7) Ratio for ADCC After culturing SKBR-3 and MCF-7 target cells, the target cells were seeded onto a 96-well V-bottom plate (Corning) at $1\times10^4$ cells/50 μL/well and then 10 μL of trastuzumab (20 μg/mL) was added per each well. PBMCs (CTL, Table 4) were quickly thawed in a 37° C. water bath and treated with DNase I for 30 minutes at room temperature. After counting the cells, an adequate number of the PBMCs were added to each well.

TABLE 4

| Data of PBMC donors | | | | |
|---|---|---|---|---|
| Sample ID # | Ethnicity | Age | Gender | ABO/PH |
| 20091026 | Caucasian | 24 | Male | A/POS |
| 20100412 | Hispanic | 30 | Male | A/POS |
| HHU20120530 | African/American | 35 | Male | AB/POS |
| HHU20130318 | Asian | 38 | Male | A/POS |
| HHU20150924 | Asian/Filipino | 40 | Male | A/POS |

Figure 11:
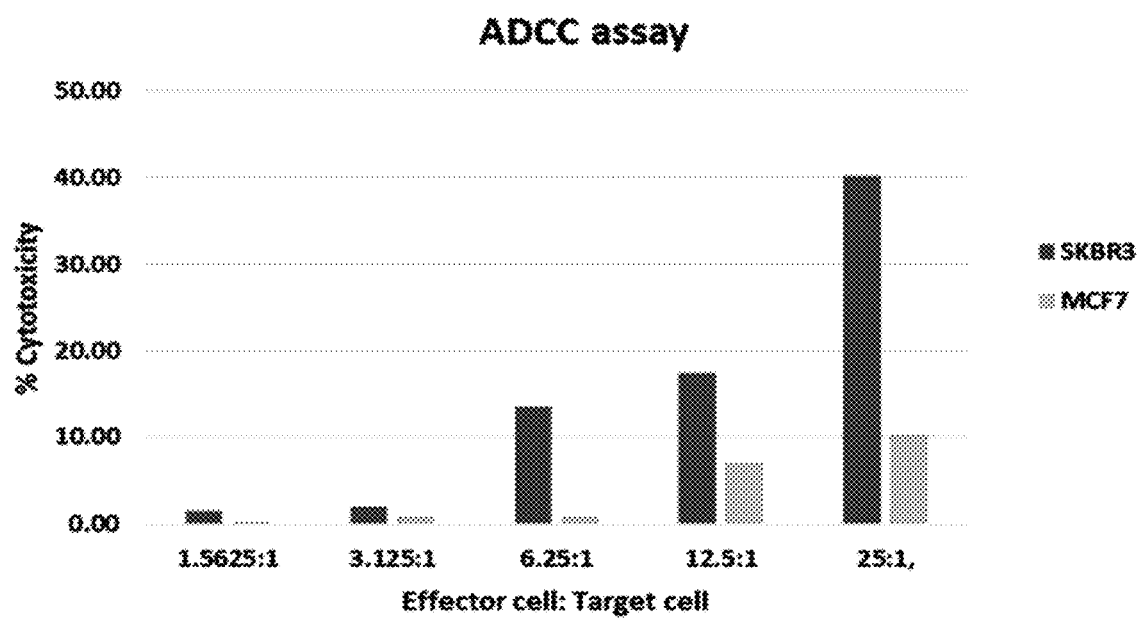
FIG. 11 shows an ADCC tendency analysis result depending on the ratio of effector cell:target cell.

The effector cell: target cell ratio was set to 1.5625:1, 3.125:1, 6.25:1, 12.5:1 and 25:1. After centrifuging at 100×g for 1 minute, the cells were cultured in a 37° C., $CO_2$ incubator for 4 hours. 4 hours later, the plate was centrifuged at 300×g for 3 minutes. 50 μL of the supernatant was taken and transferred onto a SpectraPlate 96-well plate (PerkinElmer). Then, incubation was conducted at room temperature for 30 minutes after adding 50 μL of CytoTox 96® reagent (Promega) per each well. After terminating the reaction by adding 50 μL of a stop solution, absorbance was measured at 490 nm. This procedure was repeated 3 times in duplicates and the mean value was taken. As a result, the ADCC assay using SKBR-3 ($1\times10^4$ cells/well) with high HER2 expression as target cells and using PBMC as effector cells showed effector cell number-dependent increase in cytotoxicity. Although MCF-7 with low HER2 expression also showed effector cell number-dependent increase in cytotoxicity, the increase was lower as compared to SKBR-3 exhibiting higher HER2 expression (FIG. 11). The higher cytotoxicity for SKBR-3 with high HER2 SKBR-3 than for MCF-7 with low HER2 expression suggests that the cytotoxicity is HER2-specific. In consideration of the difference in the distribution of FcγRIIIa FN variants in the PBMCs used as effector cells, it was determined that the effector cell:target cell ratio for evaluation of ADCC activity should be 25:1 or greater (Table 5).

TABLE 5

| ADCC activity depending on effector cell:target cell ratio | | |
|---|---|---|
| | % Cytotoxicity | |
| Effector:target | SKBR-3 | MCF-7 |
| 1.5625:1 | 1.65 | 0.23 |
| 3.125:1 | 2.00 | 0.98 |
| 6.25:1 | 13.54 | 1.01 |
| 12.5:1 | 17.47 | 7.00 |
| 25:1 | 40.21 | 10.38 |

Example 12

Comparison of ADCC Activity of Herceptin Variants Using Human PBMC

Figure 12:
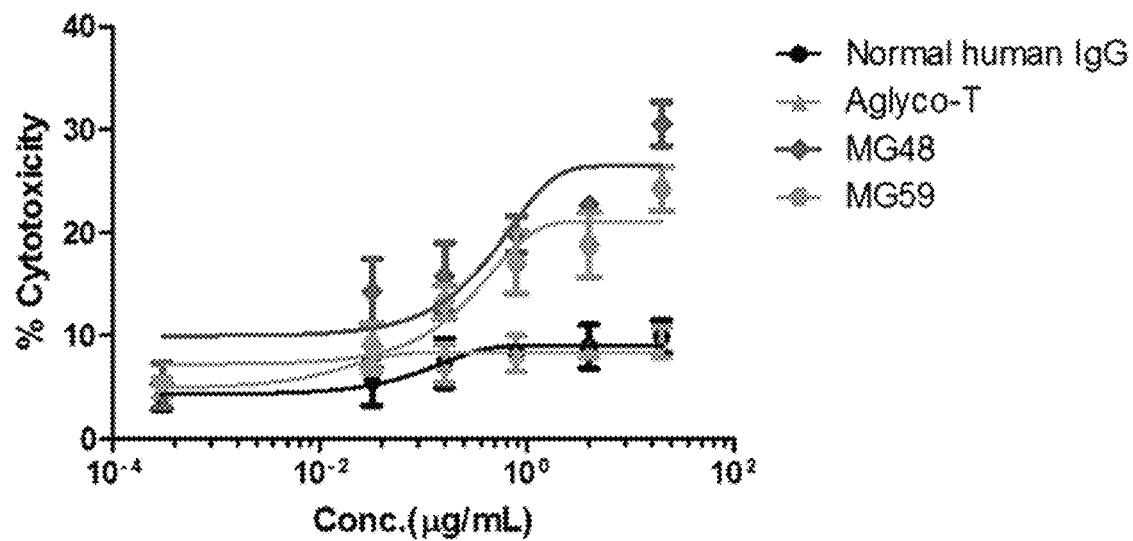
FIG. 12 shows a result of analyzing the cancer cell killing effect of variants using human PBMC, SKBR-3 and MCF-7.
Figure 12:
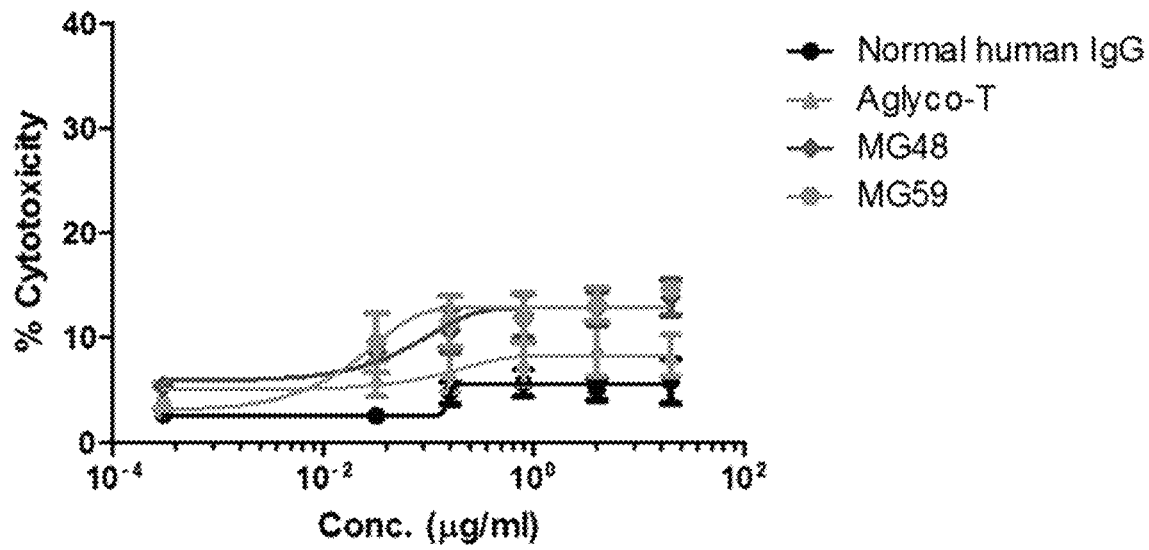

SKBR-3 and MCF-7 cells were seeded onto a 96-well plate (V-bottom) at $1\times10^4$ cells/50 μL per well, and 10 μL of the test substance was added at 0, 0.032, 0.16, 0.8, 4 and 20 μg/mL to each well. Five individual PBMC samples were quickly thawed in a 37° C. water bath and treated with DNase I for 30 minutes at room temperature. After counting the cells and adding $2.5\times10^5$ cells/50 μL of PBMC to each well, the plate was centrifuged at 100×g for 1 minute and then cultured in a 37° C. $CO_2$ incubator for 4 hours. 4 hours later, the plate was taken out and centrifuged at 300×g for 3 minutes. After taking 50 μL of the supernatant and transferred onto a SpectraPlate 96-well plate, 50 μL of CytoTox 96® reagent was added to each well and reaction was conducted at room temperature for 30 minutes. After terminating the reaction by adding 50 μL of a stop solution, absorbance was measured at 490 nm. This procedure was repeated 3 times in duplicates and the mean value was represented as % cytotoxicity. The SKBR-3 cells with HER2 expression showed high % cytotoxicity of 4-31%, whereas the MCF-7 cells with low HER2 expression showed low % cytotoxicity of 2-15%. Accordingly, it was confirmed that the cytotoxicity of the test substance is target-specific. In addition, it was confirmed that the cancer cell killing effect is improved remarkably as compared to the wild-type aglycosylated antibody and the human IgG antibody (FIG. 12).

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A polypeptide comprising a human IgG1 or IgG3 Fc domain, the Fc domain comprising the following amino acid substitutions according to the Kabat numbering system:
   a) 8 amino acid substitutions of S298G, T299A, K326I, A327Y, L328G, E382V, N390D and M428L; and
   b) one or more additional amino acid substitution selected from a group consisting of C226R, F243L, K246E, T250I, I253N, V264E, T307S, C347R, T350A, S400T and N421S.

2. The polypeptide according to claim 1, wherein the polypeptide comprises the following 9 amino acid substitutions: V264E, S298G, T299A, K326I, A327Y, L328G, E382V, N390D and M428L.

3. The polypeptide according to claim 1, wherein the polypeptide comprises the following 9 amino acid substitutions: S298G, T299A, T307S, K326I, A327Y, L328G, E382V, N390D and M428L.

4. The polypeptide according to claim 1, wherein the polypeptide comprises the following 9 amino acid substitutions: S298G, T299A, K326I, A327Y, L328G, C347R, E382V, N390D and M428L.

5. The polypeptide according to claim 1, wherein the polypeptide comprises the following 10 amino acid substitutions: V264E, S298G, T299A, K326I, A327Y, L328G, T350A, E382V, N390D and M428L.

6. The polypeptide according to claim 1, wherein the polypeptide comprises the following 10 amino acid substitutions: T250I, I253N, S298G, T299A, K326I, A327Y, L328G, E382V, N390D and M428L.

7. The polypeptide according to claim 1, wherein the polypeptide comprises the following 10 amino acid substitutions: V264E, S298G, T299A, K326I, A327Y, L328G, E382V, N390D, N421S and M428L.

8. The polypeptide according to claim 1, wherein the polypeptide comprises the following 11 amino acid substitutions: V264E, S298G, T299A, K326I, A327Y, L328G, T350A, E382V, N390D, N421S and M428L.

9. The polypeptide according to claim 1, wherein the polypeptide comprises the following 11 amino acid substitutions: C226R, F243L, K246E, S298G, T299A, K326I, A327Y, L328G, E382V, N390D and M428L.

10. The polypeptide according to claim 1, wherein the polypeptide comprising the amino acid substitutions has improved binding ability for FcγRIIIa as compared to the Fc domain with only 8 amino acids of S298G, T299A, K326I, A327Y, L328G, E382V, N390D and M428L substituted.

11. An aglycosylated antibody comprising the polypeptide according to claim 1.

12. A composition comprising the polypeptide according to claim 1, an aglycosylated antibody comprising the polypeptide.

13. The composition according to claim 12, wherein the composition is a pharmaceutical composition.

* * * * *

SEQUENCE LISTING

<160> NUMBER OF SEQ ID NOS: 28

<210> SEQ ID NO 1
<211> LENGTH: 227

<212> TYPE: PRT
<213> ORGANISM: Homo sapiens

<400> SEQUENCE: 1

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 2
<211> LENGTH: 681
<212> TYPE: DNA
<213> ORGANISM: Homo sapiens

<400> SEQUENCE: 2

```
gacaaaactc acacatgccc accgtgccca gcacctgaac tcctggggggg accgtcagtc     60 ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cacctcccgt gctggactcc    540
gacggctcct tcttcctcta cagcaagctc accgtggaca gagcaggtg gcagcagggg    600 aacgtcttct catgctccgt gatgcatgag gctctgcaca accactacac gcagaagagc    660
```
ctctccctgt ccccgggtaa a                                           681

<210> SEQ ID NO 3
<211> LENGTH: 227
<212> TYPE: PRT
<213> ORGANISM: Artificial Sequence
<220> FEATURE:
<223> OTHER INFORMATION: Antibody Fc Sequence (Fc1004)

<400> SEQUENCE: 3

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Gly Ala Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asp Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225
```

<210> SEQ ID NO 4
<211> LENGTH: 681
<212> TYPE: DNA
<213> ORGANISM: Artificial Sequence
<220> FEATURE:
<223> OTHER INFORMATION: Antibody Fc Sequence (Fc1004)

<400> SEQUENCE: 4
gacaaaactc acacatgccc accgtgccca gcacctgaac tcctgggggg accgtcagtc      60
ttcctcttcc cccaaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc aagacaaag ccgcgggagg agcagtacaa cggcgcgtac     240
cgtgtggtca gtgtcctcac cgtcctgcac caggactggc tgaatggcaa ggagtacaaa     300
tgcaaggtct ccaacaaagc cctcccagcc ccatcgaga aaaccatctc taaagccaaa      360

```
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggtgagca atgggcagcc ggagaacgac tacaagacca cacctcccgt gctggactcc    540
gacggctctt tcttcctcta cagcaagctc accgtggaca agagcaggtg gcagcagggg    600
aacgtcttct catgctccgt gttacatgag gctctgcaca accactacac gcagaagagc    660
ctctcccttg ccccgggtaa a                                              681
```

```
<210> SEQ ID NO 5
<211> LENGTH: 227
<212> TYPE: PRT
<213> ORGANISM: Artificial Sequence
<220> FEATURE:
<223> OTHER INFORMATION: Antibody Fc Sequence (A/IYG)

<400> SEQUENCE: 5
```

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Ala Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Ile Tyr Gly Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

```
<210> SEQ ID NO 6
<211> LENGTH: 681
<212> TYPE: DNA
<213> ORGANISM: Artificial Sequence
<220> FEATURE:
<223> OTHER INFORMATION: Antibody Fc Sequence (A/IYG)

<400> SEQUENCE: 6
gacaaaactc acacatgccc accgtgccca gcacctgaac tcctgggggg accgtcagtc    60
```

```
ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcgcgtac    240
cgtgtggtca gcgtcctcac cgtcctgcac caggactggc tgaatggcaa ggagtacaag    300
tgcaaggtct ccaacattta tgggccagcc ccatcgaga aaccatctc caaagccaaa    360 gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cacctcccgt gctggactcc    540
gacggctcct tcttcctcta cagcaagctc accgtggaca gagcaggtg gcagcagggg    600 aacgtcttct catgctccgt gatgcatgag gctctgcaca accactacac gcagaagagc    660 ctctcccctgt ccccgggtaa a    681
```

```
<210> SEQ ID NO 7
<211> LENGTH: 227
<212> TYPE: PRT
<213> ORGANISM: Artificial Sequence
<220> FEATURE:
<223> OTHER INFORMATION: Antibody Fc Sequence (Fc1004-IYG)

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Gly Ala Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Ile Tyr Gly Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225
```

<210> SEQ ID NO 8
<211> LENGTH: 681
<212> TYPE: DNA
<213> ORGANISM: Artificial Sequence
<220> FEATURE:
<223> OTHER INFORMATION: Antibody Fc Sequence (Fc1004-IYG)

<400> SEQUENCE: 8

```
gacaaaactc acacatgccc accgtgccca gcacctgaac tcctgggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cggcgcgtac     240
cgtgtggtca gtgtcctcac cgtcctgcac caggactggc tgaatggcaa ggagtacaaa     300
tgcaaggtct ccaacattta tggcccagcc ccatcgaga aaaccatctc taaagccaaa      360
gggcagcccc gagaaccaca ggtgtacacc ctgcccccat cccgggatga gctgaccaag     420
aaccaggtca gcctgacctg cctggtcaaa ggcttctatc ccagcgacat cgccgtggag     480
tgggtgagca atgggcagcc ggagaacgac tacaagacca cacctcccgt gctggactcc     540
gacggctctt tcttcctcta cagcaagctc accgtggaca agagcaggtg gcagcagggg     600
aacgtcttct catgctccgt gttacatgag gctctgcaca accactacac gcagaagagc     660
ctctcccctgt ccccgggtaa a                                              681
```

<210> SEQ ID NO 9
<211> LENGTH: 227
<212> TYPE: PRT
<213> ORGANISM: Artificial Sequence
<220> FEATURE:
<223> OTHER INFORMATION: Antibody Fc Sequence (MG42)

<400> SEQUENCE: 9

```
Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Glu Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Gly Ala Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Ile Tyr Gly Pro Ala Pro Ile
            100                 105                 110

Glu Lys Thr Ile Ser Lys Ala Lys Gly Gln Pro Arg Glu Pro Gln Val
        115                 120                 125

Tyr Ala Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asp Tyr Lys Thr Thr Pro Pro
                165                 170                 175

Val Leu Asp Ser Asp Gly Ser Phe Phe Leu Tyr Ser Lys Leu Thr Val
            180                 185                 190
```

```
Asp Lys Ser Arg Trp Gln Gln Gly Ser Val Phe Ser Cys Ser Val Leu
        195                 200                 205
His Glu Ala Leu His Asn His Tyr Thr Gln Lys Ser Leu Ser Leu Ser
    210                 215                 220
Pro Gly Lys
225

<210> SEQ ID NO 10
<211> LENGTH: 681
<212> TYPE: DNA
<213> ORGANISM: Artificial Sequence
<220> FEATURE:
<223> OTHER INFORMATION: Antibody Fc Sequence (MG42)

<400> SEQUENCE: 10
gacaaaactc acacatgccc accgtgccca gcacctgaac tcctgggggg accgtcagtc       60
ttcctcttcc ctccaaaacc caaggacacc ctcatgatct cccggacccc tgaggtcaca      120
tgcgtggtgg aggacgtgag ccacgaagac cctgaggtca agttcaactg gtacgtggac      180
ggcgtggagg tgcataatgc caagacaaag ccgcgggagg agcagtacaa cggcgcgtac      240
cgtgtggtca gtgtcctcac cgtcctgcac caggactggc tgaatggcaa ggagtacaaa      300
tgcaaggtct ccaacattta tgcccagcc cccatcgaga aaaccatctc taaagccaaa       360
gggcagcccc gagaaccaca ggtgtacgcc ctgcccccat cccgggatga gctgaccaag      420
aaccaggtca gcctgacctg cctggtcaaa ggcttctatc ccagcgacat cgccgtggag      480
tgggtgagta atgggcagcc ggagaacgac tacaagacca cacctcccgt gctggactcc      540
gacggctctt tcttcctcta cagcaagctc accgtggaca agagcaggtg gcagcagggg      600
agcgtcttct catgctccgt gttacatgag gctctgcaca accactacac gcagaagagc      660
ctctccctgt ccccgggtaa a                                                681

<210> SEQ ID NO 11
<211> LENGTH: 227
<212> TYPE: PRT
<213> ORGANISM: Artificial Sequence
<220> FEATURE:
<223> OTHER INFORMATION: Antibody Fc Sequence (MG48)

<400> SEQUENCE: 11

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Glu Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Gly Ala Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Ile Tyr Gly Pro Ala Pro Ile
            100                 105                 110
Glu Lys Thr Ile Ser Lys Ala Lys Gly Gln Pro Arg Glu Pro Gln Val
        115                 120                 125
Tyr Ala Leu Pro Pro Ser Arg Asp Glu Leu Thr Lys Asn Gln Val Ser
    130                 135                 140
```

Leu Thr Cys Leu Val Lys Gly Phe Tyr Pro Ser Asp Ile Ala Val Glu
145                 150                 155                 160

Trp Val Ser Asn Gly Gln Pro Glu Asn Asp Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225

<210> SEQ ID NO 12
<211> LENGTH: 681
<212> TYPE: DNA
<213> ORGANISM: Artificial Sequence
<220> FEATURE:
<223> OTHER INFORMATION: Antibody Fc Sequence (MG48)

<400> SEQUENCE: 12
gacaaaactc acacatgccc accgtgccca gcacctgaac tcctgggggg accgtcagtc      60
ttcctcttcc ctccaaaacc caaggacacc ctcatgatct cccggacccc tgaggtcaca     120
tgcgtggtgg aggacgtgag ccacgaagac cctgaggtca agttcaactg gtacgtggac     180
ggcgtggagg tgcataatgc caagacaaag ccgcgggagg agcagtacaa cggcgcgtac     240
cgtgtggtca gtgtcctcac cgtcctgcac caggactggc tgaatggcaa ggagtacaaa     300
tgcaaggtct ccaacattta tgcccagccc ccatcgaga aaaccatctc taaagccaaa      360
gggcagcccc gagaaccaca ggtgtacgcc ctgcccccat cccgggatga gctgaccaag     420
aaccaggtca gcctgacctg cctggtcaaa ggcttctatc ccagcgacat cgccgtggag     480
tgggtgagca atgggcagcc ggagaacgac tacaagacca cacctcccgt gctggactcc     540
gacggctctt tcttcctcta cagcaagctc accgtggaca agagcaggtg gcagcagggg     600
aacgtcttct catgctccgt gttacatgag gctctgcaca accactacac gcagaagagc     660
ctctccctgt ccccgggtaa a                                                681

<210> SEQ ID NO 13
<211> LENGTH: 227
<212> TYPE: PRT
<213> ORGANISM: Artificial Sequence
<220> FEATURE:
<223> OTHER INFORMATION: Antibody Fc Sequence (MG59)

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Glu Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Gly Ala Tyr
65                  70                  75                  80

Arg Val Val Ser Val Leu Thr Val Leu His Gln Asp Trp Leu Asn Gly

```
                    85                  90                  95
Lys Glu Tyr Lys Cys Lys Val Ser Asn Ile Tyr Gly Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asp Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225

<210> SEQ ID NO 14
<211> LENGTH: 681
<212> TYPE: DNA
<213> ORGANISM: Artificial Sequence
<220> FEATURE:
<223> OTHER INFORMATION: Antibody Fc Sequence (MG59)

<400> SEQUENCE: 14
gacaaaactc acacatgccc accatgccca gcacctgaac tcctgggggg accgtcagtc      60
ttcctcttcc ccccaaaacc caaggacacc ctcatgatct cccggacccc tgaggtcaca     120
tgcgtggtgg aggacgtgag ccacgaagac cctgaggtca agttcaactg gtacgtggac     180
ggcgtggagg tgcataatgc caagacaaag ccgcgggagg agcagtacaa cggcgcgtac     240
cgtgtggtca gtgtcctcac cgtcctgcac caggactggc tgaatggcaa ggagtacaaa     300
tgcaaggtct ccaacattta tgcccagccc ccatcgaga aaaccatctc taaagccaaa     360
gggcagcccc gagaaccaca ggtgtacacc ctgcccccat cccgggatga gctgaccaag     420
aaccaggtca gcctgacctg cctggtcaaa ggcttctatc ccagcgacat cgccgtggag     480
tgggtgagca atgggcagcc ggagaacgac tacaagacca cacctcccgt gctggactcc     540
gacggctctt tcttcctcta cagcaagctc accgtggaca gagcaggtg gcagcagggg     600 aacgtcttct catgctccgt gttacatgag gctctgcaca accactacac gcagaagagc     660 ctctcccctgt ccccgggtaa a                                              681

<210> SEQ ID NO 15
<211> LENGTH: 227
<212> TYPE: PRT
<213> ORGANISM: Artificial Sequence
<220> FEATURE:
<223> OTHER INFORMATION: Antibody Fc Sequence (MG87)

<400> SEQUENCE: 15

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30
```

Ile Ser Arg Thr Pro Glu Val Thr Cys Val Val Asp Val Ser His
            35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Gly Ala Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Ile Tyr Gly Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
Trp Val Ser Asn Gly Gln Pro Glu Asn Asp Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Ser Val Phe Ser Cys Ser Val Leu
        195                 200                 205
His Glu Ala Leu His Asn His Tyr Thr Gln Lys Ser Leu Ser Leu Ser
210                 215                 220
Pro Gly Lys
225

<210> SEQ ID NO 16
<211> LENGTH: 681
<212> TYPE: DNA
<213> ORGANISM: Artificial Sequence
<220> FEATURE:
<223> OTHER INFORMATION: Antibody Fc Sequence (MG87)

<400> SEQUENCE: 16
gacaaaactc acacatgccc accgtgccca gcacctgaac tcctgggggg accgtcagtc        60
ttcctcttcc ctccaaaacc caaggacacc ctcatgatct cccggacccc tgaggtcaca       120
tgcgtggtgg aggacgtgag ccacgaagac cctgaggtca agttcaactg gtacgtggac       180
ggcgtggagg tgcataatgc aagacaaag ccgcgggagg agcagtacaa cggcgcgtac        240
cgtgtggtca gtgtcctcac cgtcctgcac caggactggc tgaatggcaa ggagtacaaa       300
tgcaaggtct ccaacattta tggcccagcc ccatcgaga aaccatctc taaagccaaa         360 gggcagcccc gagaaccaca ggtgtacacc ctgcccccat cccgggatga gctgaccaag       420
aaccaggtca gcctgacctg cctggtcaaa ggcttctatc ccagcgacat cgccgtggag       480
tgggtgagta atgggcagcc ggagaacgac tacaagacca cacctcccgt gctggactcc       540
gacggctctt tcttcctcta cagcaagctc accgtggaca agagcaggtg gcagcagggg       600
agcgtcttct catgctccgt gttacatgag gctctgcaca accactacac gcagaagagc       660
ctctccctgt ccccgggtaa a                                                 681

<210> SEQ ID NO 17
<211> LENGTH: 49
<212> TYPE: DNA
<213> ORGANISM: Artificial Sequence
<220> FEATURE:

<223> OTHER INFORMATION: Synthetic primer (MJ#36)

<400> SEQUENCE: 17
cgcagcgagg cccagccggc catggcggag gttcaattag tggaatctg          49

<210> SEQ ID NO 18
<211> LENGTH: 43
<212> TYPE: DNA
<213> ORGANISM: Artificial Sequence
<220> FEATURE:
<223> OTHER INFORMATION: Synthetic primer (MJ#43)

<400> SEQUENCE: 18
ggacgctgac cacacggtac gcgctgttgt actgctcctc ccg                43

<210> SEQ ID NO 19
<211> LENGTH: 43
<212> TYPE: DNA
<213> ORGANISM: Artificial Sequence
<220> FEATURE:
<223> OTHER INFORMATION: Synthetic primer (MJ#42)

<400> SEQUENCE: 19
cgggaggagc agtacaacag cgcgtaccgt gtggtcagcg tcc                43

<210> SEQ ID NO 20
<211> LENGTH: 42
<212> TYPE: DNA
<213> ORGANISM: Artificial Sequence
<220> FEATURE:
<223> OTHER INFORMATION: Synthetic primer (MJ#37)

<400> SEQUENCE: 20
cgcaattcgg cccccgaggc cccttaccc ggggacaggg ag                  42

<210> SEQ ID NO 21
<211> LENGTH: 58
<212> TYPE: DNA
<213> ORGANISM: Artificial Sequence
<220> FEATURE:
<223> OTHER INFORMATION: Synthetic primer (MJ#39)

<400> SEQUENCE: 21
ggttttctcg atggggctg ggccataaat gttggagacc ttgcatttgt actccttg    58

<210> SEQ ID NO 22
<211> LENGTH: 58
<212> TYPE: DNA
<213> ORGANISM: Artificial Sequence
<220> FEATURE:
<223> OTHER INFORMATION: Synthetic primer (MJ#38)

<400> SEQUENCE: 22
caaggagtac aaatgcaagg tctccaacat ttatggccca gcccccatcg agaaaacc   58

<210> SEQ ID NO 23
<211> LENGTH: 28
<212> TYPE: DNA
<213> ORGANISM: Artificial Sequence
<220> FEATURE:
<223> OTHER INFORMATION: Synthetic primer (MJ#45)

<400> SEQUENCE: 23
cgacaagaaa gttgagccca aatcttgt                                   28

```
<210> SEQ ID NO 24
<211> LENGTH: 24
<212> TYPE: DNA
<213> ORGANISM: Artificial Sequence
<220> FEATURE:
<223> OTHER INFORMATION: Synthetic primer (MJ#46)

<400> SEQUENCE: 24
cgcaattccg gcccccgagg cccc                                            24

<210> SEQ ID NO 25
<211> LENGTH: 28
<212> TYPE: DNA
<213> ORGANISM: Artificial Sequence
<220> FEATURE:
<223> OTHER INFORMATION: Synthetic primer (MJ#44)

<400> SEQUENCE: 25
acaagatttg ggctcaactt tcttgtcg                                        28

<210> SEQ ID NO 26
<211> LENGTH: 19
<212> TYPE: DNA
<213> ORGANISM: Artificial Sequence
<220> FEATURE:
<223> OTHER INFORMATION: Synthetic primer (MJ#2)

<400> SEQUENCE: 26
ctgcccatgt tgacgattg                                                  19

<210> SEQ ID NO 27
<211> LENGTH: 47
<212> TYPE: DNA
<213> ORGANISM: Artificial Sequence
<220> FEATURE:
<223> OTHER INFORMATION: Synthetic primer (MJ#49)

<400> SEQUENCE: 27
cgcagcgagc gcgcactcca tggcggaggt tcaattagtg gaatctg                   47

<210> SEQ ID NO 28
<211> LENGTH: 35
<212> TYPE: DNA
<213> ORGANISM: Artificial Sequence
<220> FEATURE:
<223> OTHER INFORMATION: Synthetic primer (MJ#50)

<400> SEQUENCE: 28
ccctaaaatc tagacctta cccggggaca gggag                                 35
```